(12) United States Patent
Omidian et al.

(10) Patent No.: US 7,988,992 B2
(45) Date of Patent: Aug. 2, 2011

(54) SUPERPOROUS HYDROGELS FOR HEAVY-DUTY APPLICATIONS

(75) Inventors: Hossein Omidian, Weston, FL (US); Jose G. Rocca, Miami, FL (US)

(73) Assignee: KOS Life Sciences Abbott Laboratories, Abbott Park, IL (US)

( * ) Notice: Subject to any disclaimer, the term of this patent is extended or adjusted under 35 U.S.C. 154(b) by 316 days.

(21) Appl. No.: 11/774,069

(22) Filed: Jul. 6, 2007

(65) Prior Publication Data

US 2008/0089940 A1    Apr. 17, 2008

Related U.S. Application Data

(60) Provisional application No. 60/818,891, filed on Jul. 6, 2006.

(51) Int. Cl.
*A61K 9/00*  (2006.01)

(52) U.S. Cl. .................. 424/451; 424/487; 424/486

(58) Field of Classification Search ................ None
See application file for complete search history.

(56) References Cited

U.S. PATENT DOCUMENTS

| | | | |
|---|---|---|---|
| 5,273,750 A | 12/1993 | Honiger et al. | |
| 5,750,585 A | 5/1998 | Park et al. | |
| 6,271,278 B1 | 8/2001 | Park et al. | |
| 6,960,617 B2 | 11/2005 | Omidian et al. | |
| 7,056,957 B2 | 6/2006 | Omidian et al. | |
| 2003/0232895 A1* | 12/2003 | Omidian et al. | 521/99 |

FOREIGN PATENT DOCUMENTS

| | | |
|---|---|---|
| WO | 03002185 | 1/2003 |
| WO | 2004/096127 | * 11/2004 |
| WO | 2004096127 | 11/2004 |

OTHER PUBLICATIONS

Chen, et al., Journal of Biomedical Materials Research 44:53-62 (1999).
Park, et al., Biodegradable Hydrogels for Drug Delivery, 1993, Technomic Pub. Co. (Table of Contents).
Ottenbrite, et al., Hydrogels and Biodegradable Polymers for Bioapplications (ACS Symposium Series, 627), 1996, Eds. (Table of Contents).
Odian, Principles of Polymerization, 3rd Edition (1991), Wiley-Interscience (Table of Contents).
Mooney, et al., Transplantation Proceedings 26:3425-3426 (1994).
Mooney, et al., Journal of Biomedical Materials Research 29:959-965 (1995).
Ishaug, et al., Journal of Biomedical Materials Research 28:1445-1453 (1994).
International Search Report for PCT/US2007/072892 mailed Apr. 27, 2009.

* cited by examiner

*Primary Examiner* — Robert A Wax
*Assistant Examiner* — Danah Al-Awadi
(74) *Attorney, Agent, or Firm* — Lisa V. Mueller; Polsinelli Shughart PC

(57) ABSTRACT

The present invention features modified superporous hydrogels (SPHs) and methods for their formation. The SPHs of the present invention are prepared by careful selection of the hydrophobic/hydrophilic reactive ingredients and by harmonizing the foaming and polymerization reactions, which results in the formation of SPHs having a homogeneous structure and favorable physical and mechanical properties, including swelling, strength, ruggedness, and resiliency. The SPHs of the present invention are particularly useful when employed in very harsh swelling environments, such as the low pH environment of the gastric fluid of the stomach, for extended periods of time.

46 Claims, 14 Drawing Sheets

SUPERPOROUS HYDROGELS FOR HEAVY-DUTY APPLICATIONS

This application claims priority to the provisional application Ser. No. 60/818,891 filed on Jul. 6, 2006.

BACKGROUND OF THE INVENTION

The present invention relates to methods for the formation of superporous hydrogels having improved physical and mechanical properties.

Superporous hydrogels (SPHs) are porous networks of hydrophilic and/or hydrophobic polymer chains. SPHs contain a multiplicity of pores with diameters in the micrometer to millimeter range, which enable them to absorb tens of times their weight of aqueous fluids in just a fraction of a minute in a manner that is independent of their size in the dehydrated state. SPH pores are interconnected in the hydrogel matrix such that absorbing fluid can move freely through the channels (capillaries). These interconnecting pores allow the SPHs to swell much faster than conventional hydrogels that have the same swelling capacity. U.S. Pat. No. 6,271,278 describes the preparation of various SPHs in detail SPHs are also described by Chen, et al., in *J. Biomed. Mater. Res.* 44:53-62, 1999.

SPHs are generally prepared based on hydrophilic monomers, including acrylic acid and its salts, acrylamide, the potassium salt of sulfopropyl acrylate, hydroxyethyl acrylate, and hydroxyethyl methacrylate. Generally, the hydrophilic or hydrophobic nature of the primary monomer can control the SPH's properties, including swelling (capacity and rate) and mechanical properties (elasticity, compressive strength, and resiliency). In the case of hydrophilic superporous hydrogels, the swelling is favored by the presence of either ions in the polymer backbone (e.g., ionic monomers) or hydrophilic functional groups in the polymer, such as, for example, hydroxyl, carboxyl, amide, and amino groups. These hydrogels can swell to a very large size in a very short period of time. In contrast to their superior swelling properties, these hydrogels frequently suffer from weak mechanical properties. Conversely, enhanced mechanical properties can be achieved with less hydrophilic superporous hydrogels at the expense of favorable swelling properties.

SPHs can be useful as drug delivery systems (DDSs; see Park et al. (*Biodegradable Hydrogels for Drug Delivery*, 1993, Technomic Pub. Co.; and in *Hydrogels and Biodegradable Polymers for Bioapplications* (*ACS Symposium Series, 627*), 1996, Eds., Ottenbrite, et al., American Chemical Society, or by Park, et al., in U.S. Pat. No. 6,271,278. SPHs used as DDSs have been employed to release pharmaceutical agents from specific locations in the body over specific periods of time. In particular, SPHs have been employed as gastric retention devices, which prolong the time an orally administered drug resides in the upper GI tract thereby improving drug absorbance. For the purpose of gastric retention, several qualities are important in SPHs. The SPH must be able to swell to a size sufficient to delay release of the SPH from the stomach via the pyloric sphincter. It is generally thought that for oral dosage forms to remain in the stomach in the fasted state, their dimensions must be 15 mm or larger. Further, fasted state gastric conditions are characterized by an environment of greatly increased mechanical and chemical stress. Accordingly, a suitable SPH must be strong enough to resist the acidic conditions in the stomach as well as the pressures that occur during stomach contractions, which can exhibit maximum pressures in the range of 100 to 130 cm $H_2O$.

One potential design for a gastric retention system involves the incorporation of a SPH inside a capsule suitable for human ingestion. Upon entering the stomach of the patient, the capsule disintegrates and releases the SPH, whereupon the SPH swells to promote gastric retention. To be used in this way, SPHs must exhibit sufficient swelling and mechanical properties to promote gastric retention None of the SPHs known in the art exhibit all of these properties. Thus, there remains a need in the art for SPHs having both adequate swelling and high-strength mechanical properties for use in a very harsh environments, such as the gastric medium of the stomach.

SUMMARY OF THE INVENTION

This invention features superporous hydrogels (SPHs) with stable physical and mechanical properties, and methods for preparing SPHs having these properties The desirable properties are achieved by controlling the hydrophilicity/hydrophobicity of the SPH structure and by harmonizing the foaming/polymerization conditions during SPH formation.

A first aspect of the invention features a method of preparing a superporous hydrogel by a) preparing a mixture that includes an ethylenically-unsaturated monomer of hydroxyethyl methacrylate (HEMA), at least one cross-linking agent, and at least one property-modifying agent, in which the HEMA is present in the mixture in an amount greater than 80 wt %; and b) causing polymerization of the mixture by contacting it with at least one polymerization agent (e.g., a thermal initiator or an agent that produces an oxidation-reduction reaction) to form the hydrogel. In a preferred embodiment, the property-modifying agent has an ion-complexable site. In another preferred embodiment, the mixture of step a) includes at least one property-modifying agent has an ion-complexable site comprising an ion selected from (e.g., $H^+$, $Na^+$, $K^+$, $NH_4^+$ $Ca^{2+}$, $Mg^{2+}$, $Ba^{2+}$, $Cu^{2+}$, $Zn^{2+}$, $Mn^{2+}$, $Fe^{2+}$, $Fe^{3+}$, $Cr^{3+}$, $Al^{3+}$, or $Ce^{4+}$).

In one embodiment, the property-modifying agent is selected from a monomer, e.g., an acrylic acid; a polymer; and a polyphenolic complexing agent.

In yet other embodiments, the mixture of step a) further includes one or more of a diluent, a foaming agent, a foaming aid, and a foam-stabilizer. The foaming agent can be added as a solid mass; dissolved in an aqueous or organic/aqueous solvent system; dispersed in an organic solvent; coated with an organic compound such that dissolution of said foaming agent in water is delayed; encapsulated such that dissolution of said foaming agent in water is delayed; or dispersed in a monomer that participates in the superporous hydrogel polymerization. Polymerization of the hydrogel includes subjecting the mixture to foaming conditions substantially concurrently with gelation of the hydrogel.

In another embodiment, the mixture of step a) further includes a foaming agent and a foaming aid, in which the foaming aid reacts with the foaming agent within between 5 and 15 seconds after its addition to the mixture. In another preferred embodiment, the mixture of step a) can additionally include one or more ethylenically unsaturated comonomers, which are present in the mixture in less than 20 wt %.

In another embodiment, the polymerization step b) occurs at a temperature in the range of about 20° C. to about 100° C. In another embodiment, the temperature is in the range of about 55° C. to about 75° C. Alternatively, the temperature can be in the range of about 30° C. to about 60° C.

In an embodiment of the first aspect of the invention, the method further includes c) reacting the hydrogel with one or more ions (e.g., $H^+$, $Na^+$, $K^+$, $NH_4^+$ $Ca^{2+}$, $Mg^{2+}$, $Ba^{2+}$, $Cu^{2+}$, $Zn^{2+}$, $Mn^{2+}$, $Fe^{2+}$, $Fe^{3+}$, $Cr^{3+}$, $Al^{3+}$, or $Ce^{4+}$) under equilibrating conditions. Preferably, at least one ion is used that was not used in step a), or, if the same mixture of ions is used in steps a) and c), the ratio of ions used in the steps is different. The mixture of step c) can also include a chelating agent, e.g., a monovalent, bivalent, or trivalent ion salt). In particular, the chelating agent can be selected from potassium chloride, calcium chloride, and aluminum chloride.

In another preferred embodiment, after step (c), the hydrogel may further be treated with one or more ions (e.g., $H^+$, $Na^+$, $K^+$, $NH_4^+$ $Ca^{2+}$, $Mg^{2+}$, $Ba^{2+}$, $Cu^{2+}$, $Zn^{2+}$, $Mn^{2+}$, $Fe^{2+}$, $Fe^{3+}$, $Cr^{3+}$, $Al^{3+}$, or $Ce^{4+}$) under equilibrating conditions.

During method step c), the temperature of the mixture is preferably maintained at between about 20° C. and about 80° C., more preferably between about 20° C. and about 60° C., and most preferably between about 20° C. and about 40° C.

In other embodiments, the hydrogel is dehydrated, e.g., by lyophilization. Lyophilization of the hydrogel can be performed by (a) freezing the hydrogel at a temperature in the range of 23° C. to −10° C. with a cooling rate of between about 1° C. and about 5° C. per hour; (b) maintaining the hydrogel at a temperature in the range of about −5° C. to about −20° C. for between about 16 to about 24 hours; (c) lyophilizing the sample at a temperature in the range of about −5° C. to about −20° C. and a pressure of less than about 0.2 Torr for between about 60 and about 80 hours; (d) increasing the sample temperature to between about 5° C. and about 15° C. at a rate of between about 1° C. and about 5° C. per hour; and (e) maintaining the sample at a temperature in the range of about 5° C. and about 15° C. and at a pressure of less than about 200 mTorr for between about 8 to about 48 hours. Following dehydration, the hydrogel can be encapsulated. To assist in the encapsulation process, the hydrogel can be contacted with a plasticizer (e.g., ethylene glycol, polyethylene glycol, and glycerin), following dehydration, to form a plasticized hydrogel. The plasticizer can be used in an amount of between about 1 and about 20 wt/wt % of the dried hydrogel. Preferably, the plasticized hydrogel is encapsulated in an orally-administrable capsule that includes gelatin or hydroxypropyl methylcellulose. In one embodiment, the orally-administrable capsule contains a preventative layer that serves to separate the plasticized hydrogel from the capsule. In this way, the preventative layer prevents migration and/or direct contact of the plasticized hydrogel with the capsule In a preferred embodiment, the plasticized hydrogel is treated with a coating agent, which can be applied to the hydrogel prior to encapsulation, which prevents the plasticizer from contacting the capsule. In another embodiment, the hydrogel can be plasticized by exposing the hydrogel to a high relative humidity environment (e.g., greater than about 60% relative humidity) and at a temperature above about 37° C. (e.g., a temperature about 40° C. about 50° C. or about 60° C.). Preferably, the hydrogel includes a fast moisture-absorptive agent that catalyzes plasticization of the hydrogel.

A second aspect of the invention features a superporous hydrogel prepared by the method of the first aspect of the inventions. In a preferred embodiment, the hydrogel exhibits improved strength and mechanical properties (e.g., the ability to resist a compressive load of between about 2 to about 50 N; and the ability, when in its fluid-swollen state, to maintain its mechanical integrity at a pH less than about 5.0, more preferably less than about 3.0, and most preferably less than about 1.0, preferably for greater than 1 hour and most preferably for greater than 3 hours). In another embodiment, the hydrogel, when it its dry state, has an average pore size in the range of about 1 μm to about 5000 μm, preferably in the range of about 10 μm to about 3000 μm.

In other embodiments, the relative compressive strength of the superporous hydrogel is about 5-fold greater than the compressive strength of a superporous hydrogel lacking a property-modifying agent and the compressive strength at breaking point of the superporous hydrogel, when in its fluid-swollen state, is between about 1.0 kPa and about 500 kPa, more preferably between about 100 kPa and about 500 kPa. Preferably, the equilibrium volume swelling ratio of the superporous hydrogel is in the range of about 8 to 18 (swollen: unswollen).

A third aspect of the invention features a pharmaceutical composition in solid dosage form that includes a pharmacologically effective dose of a biologically active agent and the superporous hydrogel prepared by the method of the first aspect of the invention. In preferred embodiments, the biologically active agent is a drug, a nutritional supplement, or a fertilizer and the solid dosage form can be selected from a tablet, a capsule, particles, a wax, oil, granules, a film, a sheet, a fiber, a rod, and a tube. In a preferred embodiment, the tablet or capsule is formed by a molding, by direct compression, or by using a press coating compression technique.

A fourth aspect of the invention features a method for prolonged retention of a pharmaceutical agent (e.g., a drug or a nutritional supplement, such as a vitamin) by gastric retention. The method includes administering to a patient a superporous hydrogel prepared by the method of the first aspect of the invention that includes the pharmaceutical agent; the hydrogel swells upon entering the stomach of the patient and extends release of the agent for at least one hour.

By "about" is meant ±10% of the stated value.

By "cation-complexable site" is meant a position in a molecule capable of forming a reversible association with another molecule, an atom, or an ion through a non-covalent chemical bond.

By "crosslinking agent" is meant a molecule able to form a chemical bond to another substrate in the formation of a matrix.

By "hydrogel" is meant a crosslinked polymer network that is not soluble in water but swells to an equilibrium size in the presence of aqueous fluids.

By "peptide" is meant a molecule that contains from 2 to 100 natural or unnatural amino acid residues joined by amide bonds formed between a carboxyl group of one amino acid and an amino group from the next one. When referring to a crosslinking agent, the term "functionalized peptide" refers to those peptides that have at least two groups suitable for carrying out a crosslinking reaction. These groups include olefins, carbonyls, esters, acyl halides, alkyl halides, and the like.

By "protein" is meant a molecule that contains greater than 100 natural or unnatural amino acid residues joined by amide bonds formed from a carboxyl group of one amino acid and an amino group from the next one. When referring to a crosslinking agent, the term "functionalized protein" refers to those proteins that have at least two groups suitable for carrying out a crosslinking reaction. These groups include olefins, carbonyls, esters, acyl halides, alkyl halides, and the like.

By "superporous hydrogel" is meant a hydrogel that has interconnecting pores. The pores can be in excess of 1 μm, 10 μm, 100 μm, 200 μm, 300 μm, 400 μm, 500 μm, or up to the millimeter range.

DETAILED DESCRIPTION

Figure 1:
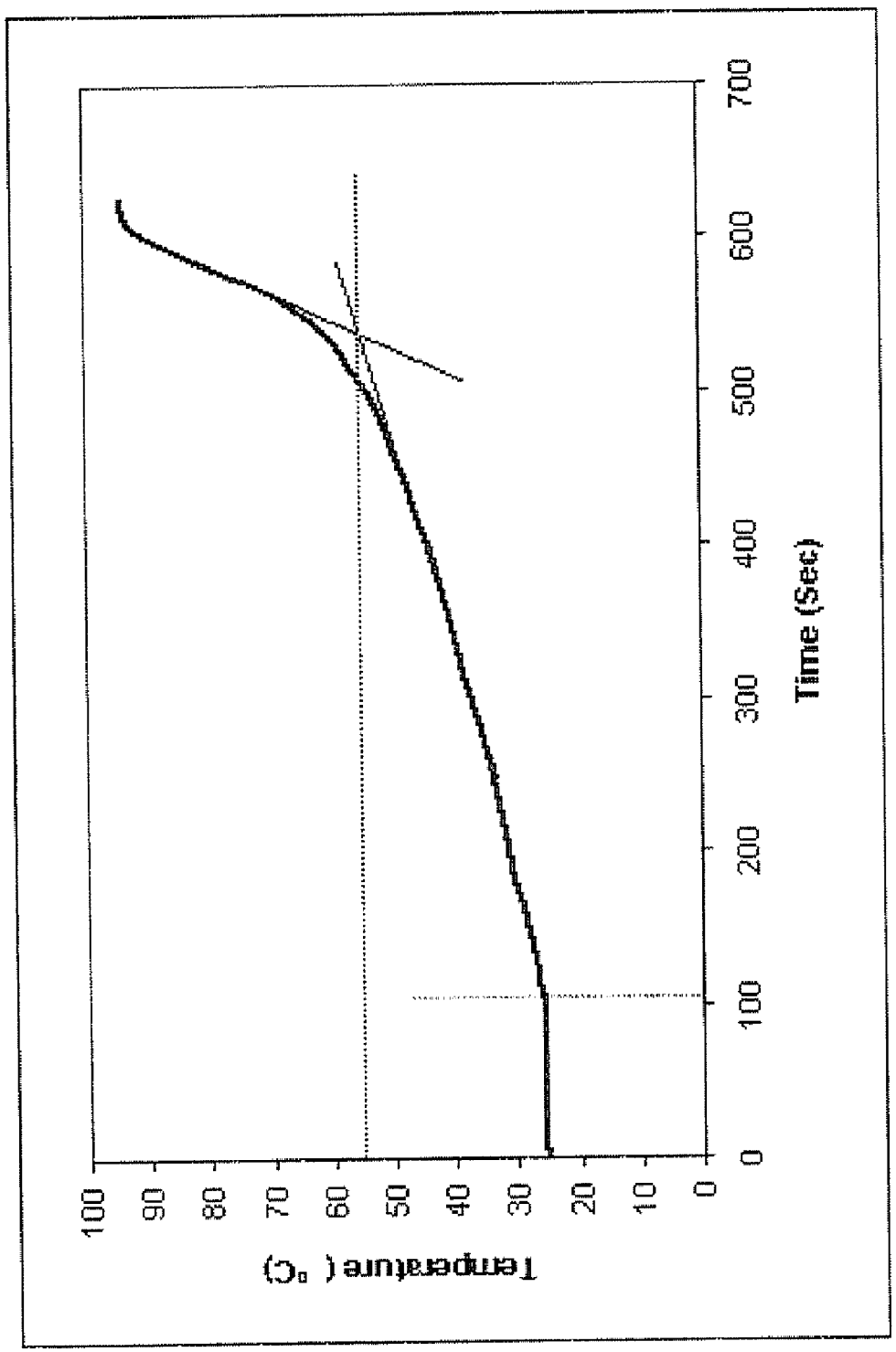
FIG. 1 is a graph showing the time/temperature profile obtained during formation of a SPH based on a formulation containing hydroxyethyl methacrylate (HEMA, 2000 μL), polyethyleneglycol diacrylate (PEGDA, 40 µL), acrylic acid (50 µL), acetic acid (40 µL), F127-10% (250 µL), tetramethyl ethylenediamine (TMED-40%, 65 µL), water (200 µL), and ammonium persulfate (APS-10%, 250 µL).

The present invention features SPHs having unique mechanical properties and swelling ability (e.g., high compressive strength with minimal diffusion and maximum capillary absorption during absorption of fluids). The SPHs of the present invention are prepared using a less hydrophilic monomer, e.g., hydroxyethyl methacrylate (HEMA) or similar, which can provide a sponge like material with certain beneficial hydrogel properties via a reduction in the absorption of water. As with other superporous hydrogel formulations, the HEMA monomer can be formulated to polymerize at room or high temperature using, e.g., thermal or redox polymerization initiators. In order to compensate for the swelling property, SPH formulations of the present invention can contain high amounts of crosslinker, which produces SPHs having an enhanced elastic property in their swollen state. To further improve the SPH properties (swelling and mechanical), a property modifier having chelating ability can be incorporated into the hydrogel network as a minor component. Adjusting the temperature at which the polymerization reaction is started also improves the porous structure and homogeneity of the SPH.

The SPHs of the present invention, which are modified polyHEMA SPHs, exhibit improved mechanical integrity and swelling abilities for extended periods of time (e.g., 1 to 5 hours) at all pH values tested, but especially when tested in a very harsh swelling environment, such as simulated gastric fluid (SGF) at a pH of 1.0.

The dehydrated SPHs of the present invention rapidly swell to a relatively large size when placed in contact with aqueous fluids, yet remain mechanically strong in their swollen state over prolonged periods of time, e.g., up to 4 hours. The present invention features methods for the preparation of these SPHs, which include choosing proper formulation and reaction conditions to obtain a very strong and non-reflexive SPH. The SPHs of the present invention, in their fully swollen state, are able to resist static and dynamic loadings in the range of 0.1 to 50 Newtons, the higher range being well above the requirements for all but the most rigorous pharmaceutical or biomedical applications.

Thus, the SPHs of the present invention possess superior chemical and mechanical integrity as compared to SPHs of the prior art while being pH independent (reduced pH sensitivity). As such, the SPHs of the present invention can be effectively used for gastric retention drug delivery, particularly within the harsh environment of a fasted state.

Superporous Hydrogel Formation

To prepare a SPH of the invention, an ethylenically-unsaturated monomer, preferably 2-hydroxyethyl methacrylate (HEMA), is mixed with one or more of the following components: one or more co-monomers comprising ion-complexable sites one or more crosslinkers, diluents, surfactants, foaming agents, foaming aids, and initiators, to form a polymerization reaction. In a preferred embodiment, the HEMA is present in the mixture in an amount of 80 wt % or greater, e.g., 85, 90, or 95 wt %. The mixture may also include ionic polysaccharides and can be polymerized by any method known to those skilled in the art, e.g., the methods described by Odian in *Principles of Polymerization*, 3$^{rd}$ Edition (1991), Wiley-Interscience. Polymerization techniques can include, for example, solution, suspension, microsuspension, inverse suspension, dispersion, emulsion, microemulsion, and inverse emulsion polymerization.

The ethylenically-unsaturated comonomer used to make the superporous hydrogel of the invention can be acrylic acid (AA) and salts thereof, $C_{1-6}$ alkyl esters of acrylic acid and salts thereof, methacrylic acid and salts thereof, $C_{1-6}$ alkyl esters of methacrylic acid, acrylamide (AM), $C_{1-6}$ methacrylic acid and salts thereof, $C_{1-6}$ alkyl esters of methacrylic acid, acrylamide (AAm), $C_{1-6}$ alkylamides of acrylic acid, $C_{2-12}$ dialkylamides of acrylic acid, N-isopropylacrylamide (NIPAM), methacrylamide, $C_{1-6}$ alkylamides of methacrylic acid, $C_{2-12}$ dialkylamides of methacrylic acid, N-cyclopropyl methacrylamide, N,N-dimethylaminoethyl acrylate, acrylonitrile, 2-hydroxyethyl acrylate (HEA), ethyl acrylate, butyl acrylate, isodecyl methacrylate, methyl methacrylate, lauryl methacrylate, stearyl methacrylate, 2-hydroxypropyl acrylate, 2-hydroxypropyl methacrylate (HPMA), butanediol monoacrylate, itaconic acid, N-vinyl pyrrolidone (VP), N,N-dimethylaminoethlyl acrylate, dialkyldimethylammonium chloride (DADMAC), 2-(methacryloyloxy)ethyl trimethylammonium chloride, 2-acrylamido-2-methyl-1-propanesulfonic acid (AMPS), potassium 3-sulfopropyl acrylate (SPAK), potassium 3 sulfopropyl methacrylate (SPMAK), or 2-(acryloyloxyethyl)trimethylammonium methyl sulfate (ATMS). Preferably, the comonomer is AAm, NIPAM, HEA, AAc or salts thereof, methacrylic acid or salts thereof, DADMAC, or SPMAK. More preferably, the mixture includes a combination of acrylic acid and HEA comonomers.

Desirably, the concentration of comonomer is from about 0.5% to about 20% (v/v), preferably about 5% to about 15% (v/v), and most preferably about 10% (v/v), of the total reaction mixture when present. Most desirably, the reaction mixture includes 2-hydroxymethyl methacrylate (HEMA) as a primary monomer and a comonomer selected from one or more of AAm, NIPAM, Methacrylic Acid, AAC, or salts thereof, DADMAC, or SPMAK.

Crosslinking agents can be N,N'-methylenebisacrylamide (BIS), N,N'-ethylenebisacrylamide (EBA), polyethylene glycol diacrylate (PEGDA), polyethylene glycol dimethacrylate (PEGDMA), ethylene glycol diglycidyl ether, alkoxylated cyclohexanedimethanol diacrylate, dipentaerythritol pentaacrylate, ethoxylated (9) trimethylolpropane triacrylate, ethoxylated (15) trimethylolpropane triacylate, methoxy polyethylene glycol (550) monomethacrylate, ethoxylated hydroxyethyl methacrylate, methoxy polyethylene glycol (350) methacrylate, glycidyl methacrylate, polyamidoamine epichlorohydrin resin, trimethylolpropane triacrylate (TMPTA), piperazine diacrylamide, glutaraldehyde, or epichlorohydrin, as well as degradable crosslinking agents, including crosslinkers containing 1,2-diol structures (e.g., N,N'-diallyltartardiamide and ethylene glycol dimethacrylate), and functionalized peptides or proteins (e.g., albumin modified with vinyl groups). Desirably, the volume/volume ratio of crosslinker to monomer is from about 0.01/100 to about 1/10. Most desirably, the volume/volume ratio of crosslinker to monomer is from about 1/100 to 5/100. Desirably, the crosslinker is PEGDA.

Diluents that can be used to form a SPH of the present invention include deionized water (DI) any organic solvent in water, or any alcohol, including, e.g., ethyl alcohol and isopropyl alcohol (IPA). Useful organic solvents include methanol, ethanol, 1-propanol, 2-propanol, tetrahydrofuran, dioxane, formic acid, acetic acid, acetonitrile, nitromethane, acetone, or 2-butanone. Desirably, the non-aqueous solvent is ethanol.

In the synthesis of a SPH of the present invention, the foaming and polymerization reactions occur simultaneously or nearly simultaneously. Thus, controlling the timing of these reactions is important. To promote foaming by chemical means, a foaming agent, which is defined as any substance or combination of substances capable of producing a cellular, structure within a polymer matrix, is brought into contact with a foaming aid. Preferably, the foaming agent will start to react with the foaming aid in the mixture within about 5 to about 15 seconds after the addition of the foaming agent. A foaming agent can be added to the reaction mixture as a solid mass or it can be dissolved in an aqueous or organic/aqueous solvent system; dispersed in an organic solvent; coated with an organic compound such that dissolution of the foaming agent in water is delayed; encapsulated such that dissolution of the foaming agent in water is delayed; or dispersed in a monomer that participates in polymerization of the SPH.

Foaming agents include physical agents that expand when pressure is released, such as nitrogen and carbon dioxide, and chemical agents, which decompose or react, e.g., in the presence of an acid, to form a gas, e.g., azodiacarbonamide, $NaHCO_3$, $Na_2CO_3$, and $CaCO_3$. Inorganic carbonates, such as sodium carbonate, potassium carbonate, ammonium carbonate, calcium carbonate, potassium bicarbonate, ammonium bicarbonate, or, most desirably, sodium bicarbonate, are preferred for use as a foaming agent. Desirably, the weight (in mgs) to volume (in μL) ratio of foaming agent to monomer is from about 0.1/100 to about 2/5. Most desirably, the w/v ratio of foaming agent to monomer is about 1/7, Foaming aids are used in combination with the foaming agent for the generation of gas. Foaming aids include organic and inorganic acids, such as, for example, acrylic acid, citric acid, acetic acid, phosphoric acid, carbonic acid, boric acid, sulfuric acid, p-toluene sulfonic acid, nitric acid, hydrobromic acid, chloric and hydrochloric acid. An example of a preferred foaming aid is glacial acetic acid. Desirably, the volume/volume or weight (in mgs) to volume (in μL) ratio of foaming aid to monomer is from about 0.01/100 to about 1/10. Most desirably, the v/v or w/v ratio of foaming aid to monomer is from about 1/100 to 5/100.

The SPH reaction mixture can also include one or more property-modifying agents, e.g., agents that contain cation-complexable sites. Property-modifying agents include, e.g., monomers, such as acrylic acid, polymers (e.g., a polysaccharide selected from alginate and derivatives thereof, chitins, chitosan and derivatives thereof, cellulose and derivatives thereof, starch and derivatives thereof, cyclodextrin, dextran and derivatives thereof, gums, lignins, pectins, saponins, deoxyribonucleic acids, and ribonucleic acids; a polypeptide or protein selected from albumin, bovine serum albumin, casein, collagen, fibrinogen, gelatin and derivatives thereof, gliadin, sodium glycine carbonate, bacterial cell membrane enzymes, and a poly(amino acid), in particular polyproline, poly(L-arginine), poly(L-lysine), polysarcosine, poly(L-hydroxyproline), poly(glutamic acid), poly(S-carboxymethyl-L-cysteine), and poly(aspartic acid); and a homo- or co-polymer comprised of one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone), and polyphenolic complexing agents. Preferred polymers include natural and synthetic polyelectrolytes, hydrophilic polymers having a net neutral charge and a molecular weight in the range of 400 Da to 40 kDa, molecules having reacting groups capable of forming complexes with multivalent cations (e.g., a carboxyl group capable of complexing with calcium, iron, or aluminum ions), deoxyribonucleic acids, and ribonucleic acids. The polymer, can also be selected from a homo- or co-polymer comprised of a monomer selected from the group consisting of acrolein potassium, (meth)acrylamides, (meth) acrylic acid and salts thereof, (meth)acrylates, acrylamide, acrylonitrile, ethylene, ethylene glycol, styrene sulfonate, aspartic acid, lysine, ethyleneimine, ethyleneoxide, styrene sulfonate, vinyl acetate, vinyl alcohol, vinyl chloride, CARBOPOL, vinylpyrrolidone, and ultramylopectin.

In yet other embodiments, the property-modifying agent is selected from carboxymethylcellulose, alginate, starch glycolate, carboxymethyl starch, dextran, pectinate, xanthan, carrageenan, gellan, hyaluronic acid, and pectinic acid, or salts thereof, wherein the salt includes a counterion selected from $Na^+$, $K^+$, $NH_4^+$ $Ca^{2+}$, $Mg^{2+}$, $Ba^+$, $Cu^{2+}$, $Zn^{2+}$, and $Mn^{2+}$, and poly(acrylic acid) and its salts, poly(methacrylic acid) and its salts, polyacrylamide, poly(styrene sulfonate), poly (aspartic acid), polylysine, CARBOPOL, and ultramylopectin.

Preferred polysaccharides include, e.g., ionic polysaccharides having negatively/positively charged groups that can counter the positive/negative charge of a cation/anion. Ordinarily, a primary cation is initially provided with the ionic polysaccharide of the SPH formulation, with the polysaccharide playing a critical role in the process of subsequent ion-equilibration(s). Preferably, the polysaccharide is chosen from the list that includes alginate and derivatives thereof, chitins, chitosan and derivatives thereof, cellulose and derivatives thereof, such as carboxymethylcellulose, starch and derivatives thereof, such as starch glycolate and carboxymethyl starch, dextran and derivatives thereof, such as cyclodextrin and dextran sulfate, gums, lignins, pectins, pectinate, saponins, hyaluronic acid, xanthan, carrageenan, gellan, and alginate, or a salt thereof, wherein the salt comprises a counterion selected from $Na^+$, $K^+$, $NH_4^+Ca^{2+}$, $Mg^{2+}$, $Ba^{2+}$, $Cu^{2+}$, $Zn^{2+}$, and $Mn^{2+}$. Most preferably, the polysaccharide is sodium carboxymethylcellulose. The ratio of polysaccharide to total solution can be in the range of about 0.1 to about 10% w/v. Preferably, the range is about 0.2 to about 5% w/v. Most preferably, the range is about 0.2 to about 1.5% w/v.

Preferred polypeptide or proteins include albumin, bovine serum albumin, casein, collagen, fibrinogen, gelatin and derivatives thereof, gliadin, sodium glycine carbonate, bacterial cell membrane enzymes, and a poly(amino acid), such as polyproline, poly(L-arginine), poly(L-lysine), polysarcosine, poly(L-hydroxyproline), poly(glutamic acid), poly(S-carboxymethyl-L-cysteine), and poly(aspartic acid).

The polyphenolic complexing agent can be selected from any one of the following: gallotannins, ellagitannins, taragallotannins, caffetannins, proanthocyanidins, catechin, epicatechin, chlorogenic acid, and arbutin.

In the preparation of the SPH, foam stabilization can be accomplished by physical or chemical means. For example, a rapid cooling or hot drying (for example, flash drying at a high temperature under an inert atmosphere) process can be used to stabilize the foam that has been produced by a gas blowing technique. Surfactants for use in preparing the SPHs of the present invention include any composition that, when dissolved in a liquid, reduces the surface tension of the liquid to the extent that a gas can be introduced into the liquid solution of the surfactant to form a foam. Desirably, a surfactant can be used to stabilize the foam until the beginning of the gelling process. Useful surfactants include chemical surfactants, such as Triton surfactants, Tween and Span surfactants, Pluronic® surfactants (poly(ethylene oxide)-poly(propylene oxide)-poly(ethylene oxide) tri-block copolymers) (BASF), Silwet® surfactants (OSi Specialties Inc.), and sodium dodecyl sulfate (Bio-Rad Laboratories), and proteinaceous surfactants, such as albumin (Sigma Chemical Company), ovalbumin, gelatin, or combinations thereof. Preferably, Pluronic® F127 (PF127) is used Surfactant concentrations in the range of about 0.2% to about 2% (w in gms/v in mLs) of the total solution were found to be adequate. Preferably, the surfactant concentration is in the range of about 0.4% to about 1% (w in gms/v in mLs). Most preferably, the surfactant concentration is about 0.9% (w in gms/v in mLs).

Polymerization of Superporous Hydrogels

Polymerization of SPHs may be initiated by any polymerization-initiator system that is suitable for the polymerization of unsaturated monomers in the homogeneous or heterogeneous phase. In general terms, initiator systems that may be used in the process according to the present invention are those known to the person skilled in the art (see, e.g., U.S. Pat. Nos. 6,960,617; 6,271,278; and 5,750,585; and U.S. Patent Application Publication Nos. US 2003/0232895 and U.S. Pat. No. 7,056,957; each of which is incorporated herein by reference). In preferred embodiments, polymerization occurs at a temperature in the range of about 20° to about 100° C., preferably in the range of about 30° to about 60° C. Polymerization of the SPH at higher temperatures, e.g., greater than about 50° C., produces SPHs having more structural homogeneity, smaller pore sizes, more flexibility in a swollen state, faster rate of absorption, and easier and more efficient purification.

Without restricting the present invention, such polymerization initiators are desirably free-radical or free-radical forming compounds or mixtures of substances, such as, for, example, hydroperoxides, preferably cumyl hydroperoxide and tert.-butyl hydroperoxide; organic peroxides, preferably dibenzoyl peroxide, dilauryl peroxide, dicumyl peroxide, di-tert.-butyl peroxide, methyl ethyl ketone peroxide, tert-butylbenzoyl peroxide, diisopropyl peroxydicarbonate, or dicyclohexyl peroxydicarbonate, di-tert-butyl peroxalate; inorganic peroxides, preferably ammonium persulfate, potassium persulfate, potassium peroxydisulfate or, hydrogen peroxide; azo compounds, preferably azobis(isobutyronitrile), 1,1'-azobis(1-cyclohexane nitrile), 4,4'-azobis(4-cyanovaleric acid), or triphenyl-methylazobenzene; and redox systems, preferably mixtures of peroxides and amines (e.g., ammonium persulfate/sodium metabisulfite and ammonium persulfate/tetramethylethylenediamine) or mixtures of peroxides and reducing agents, optionally in the presence of metal salts and/or chelating agents.

The initiator systems can be pure or in the form of mixtures of two, three or more different initiator systems. In another example, portions of the initiator system are added to the reaction separately in solid, liquid or gaseous form. This procedure is particularly suitable for redox initiator systems. In the present invention, a combination of an oxidant and a reductant (a redox pair) is desirable as an initiator. Most desirably, the redox pair of ammonium persulfate (APS) and N,N,N',N'-tetramethylethylenediamine (TEMED) is used. Example of hydrogels prepared using a redox initiator system can be found in, e.g., U.S. Pat. No. 5,750,585, incorporated herein by reference.

Alternatively, SPH's of the present invention can be formed using a thermal initiator of polymerization, such as a thermally decomposable initiator (e.g., ammonium perfulfate).

In another preferred embodiment, the SPHs of the present invention are formed using combined thermal and redox initiator systems.

Further Modification of Superporous Hydrogels

Ion equilibration is a process by which ion exchange happens within the substrate structure. The exchange process may tale place between any kinds of ions of different valences (e.g., monovalent, divalent, trivalent or higher). For example, bivalent cations within the substrate can partially be replaced by trivalent cations or vice versa. When the process of ion-equilibration is completed, the SPH product contains equilibrium amounts of two or more cations. The equilibration just described results in considerable change in substrate properties. For example, sodium salt of carboxymethylcellulose is soluble in water, while its calcium-treated derivative is water-insoluble. Therefore, a simple partial replacement of sodium with calcium cation makes the final polymer sparingly soluble or insoluble in water. The general process of dramatically changing the properties of a substrate based on ion-exchange can also be applied to a SPH formulation of the invention.

A SPH of the present invention can originally contain ions or can be ionized after its formation. The SPH may contain a primary cation selected from a salt, ionic monomer, ionic polymer, or any other ionic ingredient. The primary cation can be subsequently partially or completely replaced by another cation, i.e., a secondary cation. An equilibrium mixture of primary and secondary cations can also be equilibrated with a third cation, i.e., tertiary cation, and so on. To achieve a desirable hydrogel property, the process of ion-equilibration can be repeated with a number of different cations. A simple salt, ionic monomer, ionic polymer or another ion source can provide the secondary or tertiary cation. The ion-equilibration process can take place in an aqueous or a mixed aqueous/alcoholic medium, where the ions can move with freedom.

After foaming and polymerization are completed, an ion-bearing SPH can be immediately placed into an aqueous or mixed aqueous/alcoholic solution that includes any monovalent, bivalent, or trivalent cations, or mixture thereof, or of higher-valent cations, e.g., cerium. Preferably, the monovalent cation is $H^+$, $Na^+$, $K^+$, or $NH_4^+$. Preferably the bivalent cation is $Ca^{2+}$, $Ba^{2+}$, $Mg^{2+}$, $Cu^{2+}$, $Zn^{2+}$, $Mn^{2+}$, or $Fe^{2+}$. Most preferably, the bivalent cation is $Ca^{2+}$. Preferably, the trivalent cation is $Fe^{3+}$, $Cr^{3+}$, or $Al^{3+}$. Normally, the ion-exchange process between monovalent and bivalent cations is rapid as fast swelling of the SPH significantly decreases the time required for this exchange/equilibration. Although the process of ion-equilibration is fast, to ensure that the ion-equilibration process has been completed, a treatment time in the range of about 0.5 hour to about 24 hours is recommended. To obtain additional desirable properties, such as improved mechanical properties, the ion-equilibrated SPH may be retreated with a solution that includes a tertiary cation. Preferably, the trivalent cation is iron or aluminum. As before with the secondary cation equilibration, the SPH is placed into medium that includes a trivalent cation and cation equilibration occurs rapidly. To ensure that ion-equilibration has been completed, the hydrogel is left in the solution for period of time, preferably from about 0.5 hour, to about 24 hours. Preferably, the equilibration process occurs at a temperature of between about 20° to about 60° C. more preferably between about 20° to about 35° C. The influence of cations on SPH properties is disclosed in, e.g., U.S. Pat. No. 7,056,957 (see Table 1).

The ion-equilibrated hydrogel is then thoroughly washed with pure water, washed with a non-aqueous, water-miscible solvent, and dried out in an oven or in a vacuum oven. Alternatively, the purified superporous hydrogel can be dried out in an oven/vacuum oven or by a lyophilization technique.

Dehydration of Superporous Hydrogels

The SPHs of the present invention are normally dehydrated and stored before use. When dehydrating a SPH by lyophilization, one method that can be utilized includes the steps of, (a) freezing the SPH sample at a temperature of about 23° C. to about −10° C. with a cooling rate of about 3° C. per hour, (b) maintaining the sample at about −10° C. for about 16 to about 24 hours, (c) lyophilizing the sample at about −10° C. and at less than about 0.2 Torr for about 60 to about 80 hours, (d) increasing the sample temperature to about 10° C. at a rate of about 3° C. per hour, and (e) maintaining the sample at about 10° C. and at less than about 200 mTorr for at least about 12 hours.

For dehydration of an ion-equilibrated SPH using a non-aqueous solvent, a desirable method includes the steps of (a) displacing water contained in the hydrogel matrix with a non-aqueous, water-miscible solvent or solvent mixture through a series, of washings, and (b) removal of the non-aqueous solvent or solvent mixture at a pressure of less than about 50 Torr or by heat. The non-aqueous solvent can include methanol, ethanol, 1-propanol, 2-propanol, tetrahydrofuran, dioxane, formic acid, acetic acid, acetonitrile, nitromethane, acetone, or 2-butanone. Preferably, the non-aqueous solvent is ethanol.

Use of Superporous Hydrogels of the Present Invention

SPHs of the invention can be used in a variety of different applications owing to the unique properties exhibited by these SPHs over other hydrogels, including other SPHs that are manufactured without the incorporation of HEMA. The SPH can be in any form, including but not limited to a film, sheet, particle, granule, fiber, rode or tube. For example, the SPHs of the present invention are extremely useful in drug delivery, desirably, for use as an oral pharmaceutical agent. Drug delivery can involve implanting a controlled release drug or drug composition within a matrix of a dehydrated SPH of the present invention. This, in turn, would be contained in a capsule (e.g., a gelatin capsule) or similar housing system that can be eroded by the acidic conditions in the stomach. The gastric retention of SPHs is based on their unique swelling properties, i.e., fast swelling to a large size. Once a SPH of the present invention is exposed to gastric fluid, it rapidly swells to its maximum swelling capacity, tropically in less than ten minutes. For their use in humans, SPHs that swell to a diameter of greater than about 2 cm at low pH conditions are desirable as they are then unable to pass through the pylorus sphincter, ensuring, prolonged residence in the stomach and better absorption of the drug.

In addition to drug delivery, the SPHs of the present invention can have a variety of other applications including, for example, tissue engineering, vascular surgery (e.g., angioplasty) and drainage (e.g., from the kidney). Devices prepared using SPHs of the present invention can include, but are not limited to vascular grafts, stents, catheters, cannulas, plugs, constrictors, tissue scaffolds, and tissue or biological encapsulants, and the like.

The SPHs of the present invention may be applied to any use that requires a porous hydrogel material, particularly a use that requires a hydrogel material having an open pore structure. For example, the materials are useful as matrices or scaffolds into which cells can migrate, the cells being compatible therein and growing to achieve their intended function, such as in tissue replacement, eventually replacing the matrix depending on its biodegradability. Furthermore, the materials can be used to provide matrices already bound to cells, which may then be surgically implanted into a body. Further, the materials can be used as wound healing matrix materials, as matrices for in vitro cell culture studies or uses similar thereto. The SPHs of the present invention are ideal for use in culturing cells owing to their stable structure.

The SPHs of the present invention may also have application in cell transplantation. For example, SPHs of the present invention can be used for the transplantation of hepatocytes (see, e.g., D. J. Mooney, P. M. Kaufmann, K. Sano, K. M. McNamara, J. P. Vacanti, and R. Langer, "Transplantation of hepatocytes using porous biodegradable sponges," *Transplantation Proceedings*, 1994, 26:3425-3426; D. J. Mooney, S. Park, P. M. Kaufmann, K. Sano, K. McNamara. J. P. Vacanti, and R. Langer, "Biodegradable sponges for hepatocyte transplantation," *Journal of Biomedical Materials Research*, 1995, 29:959-965), chondrocytes, and osteoblasts (see, e.g., S. L. Ishaug, M. J. Yaszemslci, R. Biciog, A. G. Mikos; "Osteoblast Function on Synthetic Biodegradable Polymers", *J. of Biomed Mat. Res.*, 1994, 28:1445-1453).

SPHs of the present invention can also be used to create three-dimensional tissues that include, e.g., smooth muscle cells, especially if appropriate cell adhesion ligand(s) are coupled to the SPH. In addition, the SPHs of the present invention can incorporate growth factors. Thus, the SPHs of the present invention can be used to provide a suitable environment for cell proliferation.

Another useful application for the SPHs of the present invention is for guided tissue regeneration (GTR). This application is based on the premise that progenitor cells responsible for tissue regeneration reside in the underlying healthy tissue and can be induced to migrate into a defect and regenerate the lost tissue. A critical feature of materials for GTR is the transport of cells into the material, a property which is dictated by the pore size distribution and pore continuity, i.e., interconnectivity. The material must allow the desired cells to invade the material while preventing access to other cell types.

Because of the absorbent properties of the SPHs of the present invention they are well-suited for use in absorbent articles, and especially for use as disposable absorbent articles. By "absorbent article" is meant a consumer product that is capable of absorbing significant quantities of water and other fluids (i.e., liquids), e.g., body fluids Examples of absorbent articles include disposable diapers, sanitary napkins, incontinence pads, paper towels, facial tissues, and the like.

SPHs of the present invention axe also useful for protecting, holding or transplanting growing plants in the form of seeds, seedlings, tubers, cuttings, nursery stock, roots, transplants and the like. These SPHs can aid a growing plant, either alone or in combination with fertilizer, agricultural modified minerals, and the like uniformly dispersed throughout.

SPHs of the present invention are also useful for adsorption, extraction, separation, and filtration purposes. For example, the SPHs can be used as a desiccant to remove moisture from the surrounding environment. The SPHs of the present invention can be used to separate water from mixtures containing, e.g., mixed water/oil, water/alcohol, water/organic solvents, and similar.

Characteristics of Superporous Hydrogels of the Present Invention

SPHs of the present invention exhibit several improved characteristics, including, ergs, prolonged stable swelling and mechanical properties in their swollen state (egg when swollen in very harsh swelling medium, such as stimulated gastric fluid), and structural homogeneity. The equilibrium volume swelling ratio of SPHs of the present invention falls within the range of about 8 to about 18 (swollen volume to unswollen volume).

SPHs of the present invention can also withstand greater compressive loads, e.g., a compressive load of 10 N or greater (e.g., a compressive load in the range of about 10 N to about 50 N). The SPHs of the present invention also retain their mechanical integrity under the swelling conditions found in the environment of the stomach, i.e., swollen with gastric fluid, and the compressive loads applied by the stomach. In a preferred embodiment, the SPH can retain its mechanical integrity at a pH of less about 5.0, more preferably at a pH of about 3.0, and most preferably at a pH of about 1.0, for at least greater than one hour and more preferably for greater than three hours. In a preferred embodiment, the SPHs of the present invention that include one or more property-modifying agents, such as the ones described above, can withstand a compressive load of at least about 5-fold greater, more preferably at least about 10-fold greater, and most preferably at least about 20-fold greater, than SPHs prepared without the property-modifying agent(s).

In other embodiments, the SPHs of the present invention exhibit an average pore size of about 1 μm to about 5,000 μm. More preferably, the SPHs exhibit an average pore size of about 10 μm to about 3,000 μm. The pore size of the SPH critically affects the SPH properties. Conditions such as higher reaction temperature, higher water content of the reacting medium, and higher concentration of foaming components results in a taller foam with higher swelling, better processability, and lower mechanical properties in the swollen state. A shorter foam exhibits larger pore sizes and more rigidity in the swollen state.

The methods of the present invention yield a very processable polyHEMA-based SPH product that can be prepared using a high starting reaction temperature. The SPH can be processed into a very thin hydrogel in its swollen form.

The preparation of an polyHEMA SPH of the present invention using a high starting reaction temperature results in a very homogeneous porous structure having smaller pores, more flexibility in the swollen state, and faster absorption rates, and which can be easily purified. The polyHEMA SPH of the present invention behaves like a sponge for water and absorbs water mostly via a capillary mechanism.

The following non-limiting examples are illustrative of the present invention.

EXAMPLES

Example 1

Harmonized Foaming and Gelation in the Manufacture of Superporous Hydrogels

In order to prepare a SPH of the present invention, the foaming and polymerization reactions are simultaneously controlled ('harmonized'). This is done by monitoring the time/temperature profile during SPH formation and noting the progress of the foaming process. In one example, based on a formulation containing hydroxyethyl methacrylate (HEMA, 2000 μL), polyethyleneglycol diacrylate (PEGDA, 40 μL), acrylic acid (50 μL), acetic acid (40 μL) F127-10% (250 μL), tetramethyl ethylenediamine (TMED-40%, 65 μL), water (200 μL), and ammonium persulfate (APS-10%, 250 μL), the temperature/time profile shown in FIG. 1 was obtained.

As indicated by Table 1 and FIG. 1, the temperature of this profile starts at 25° C. After an induction period of about 100 sec, the reaction starts and continues smoothly over the next 400 sec, with a linear increase of temperature to about 55° C. During this time it was observed that the viscosity of the reaction mixture increased slightly. The reaction then becomes vigorous, with a sharper linear increase in temperature over the next 100 seconds. During this time the solution turns quickly to a turbid mass. The SPH prepared using this formulation exhibits improved strength and mechanical properties.

TABLE 1

Time and Temperature Profile of SPH Gelation

| Time Min. Sec | Temp. ° C. |
|---|---|
| 0.0 | 25 |
| 1.42 | 25.1 |
| 1.53 | 25.3 |
| 2.03 | 25.5 |
| 2.21 | 26.6 |
| 2.27 | 27.3 |
| 2.41 | 28 |
| 2.59 | 29 |
| 3.19 | 30 |
| 3.34 | 31 |
| 3.49 | 32 |
| 4.10 | 33 |
| 4.58 | 36 |
| 6.01 | 40 |
| 7.04 | 45 |
| 7.48 | 50 |
| 8.22 | 55 |
| 8.42 | 60 |
| 8.56 | 65 |

TABLE 1-continued

Time and Temperature Profile of SPH Gelation

| Time Min. Sec | Temp. ° C. |
|---|---|
| 9.04 | 70 |
| 9.12 | 77.3 |
| 9.19 | 83.3 |
| 9.26 | 88.9 |
| 9.35 | 92.9 |
| 9.45 | 95.2 |

The profile was exploited to prepare a polyHIEMA SPH at room temperature. Sodium bicarbonate (SBC) as the foaming agent was added after about 2 min followed by the addition of ammonium persulfate (APS). The SBC dispersion was continued during the increase in viscosity. The SPH foam was left in 5 wt % aluminum chloride solution for about 20 minutes. The final SPH was a very strong and homogeneous foam, which exhibited improved mechanical properties in the swollen state.

Figure 3:
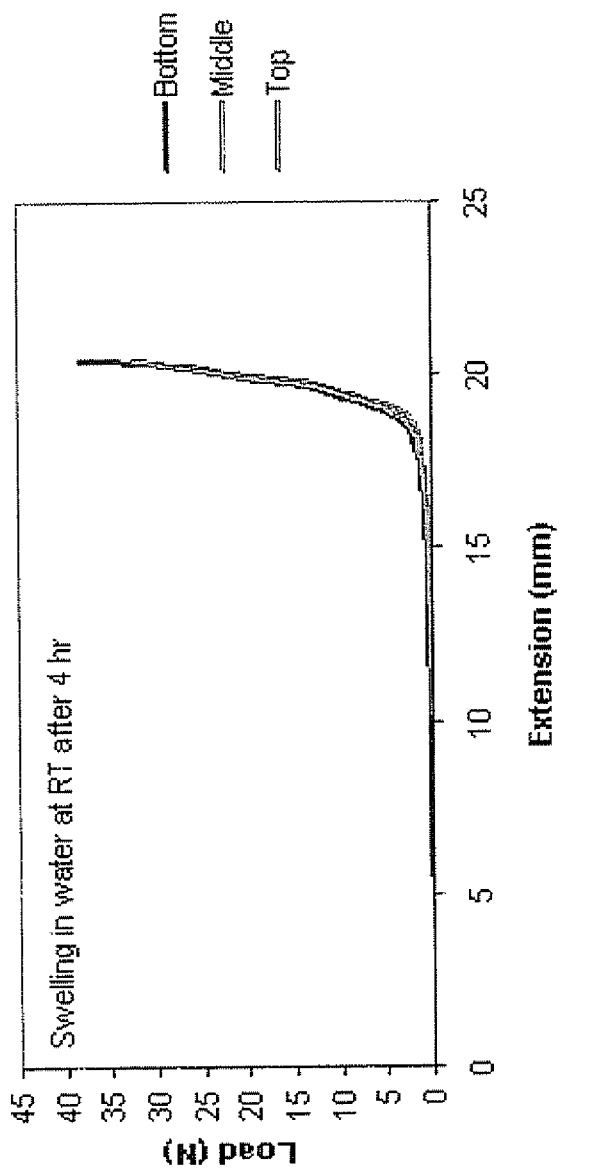
FIG. 3 is a graph showing SPH mechanical property and homogeneity for a p(HEMA)-based SPH synthesized at a starting reaction temperature of 60° C., and swelling for 4 hours in a deionized water swelling mediums.

FIG. 3 is a graph showing the results of an evaluation of a pHEMA SPH prepared by the method described above, except that the SPH was prepared at a starting reaction temperature of 60° C. The SPH, once formed, was tested using a Chatillon TCD-200 digital mechanical tester. The SPH was swollen using deionized water as the swelling medium at a temperature of 22-25° C. The SPH was retained in the swelling medium for at least 4 hrs before mechanical testing.

Testing of the SPH was as follows: a cylindrical dehydrated SPH sample was placed into water at RT for about 4 hrs. The fully swollen gel was subjected to the mechanical testing. Top, middle and bottom parts of the swollen gel were tested and proved to offer the same mechanical properties under compression During synthesis, the carbon dioxide gases travel upward, while the gelation process in ongoing A very homogenous SPH is produced by avoiding the presence of different concentrations of $CO_2$ gases in different parts of the gel during gelation; the presence of different concentrations of $CO_2$ gases in different parts of the gel during gelation results in a SPH exhibiting non-homogeneous swelling and mechanical properties, which are to be avoided.

Figure 4:
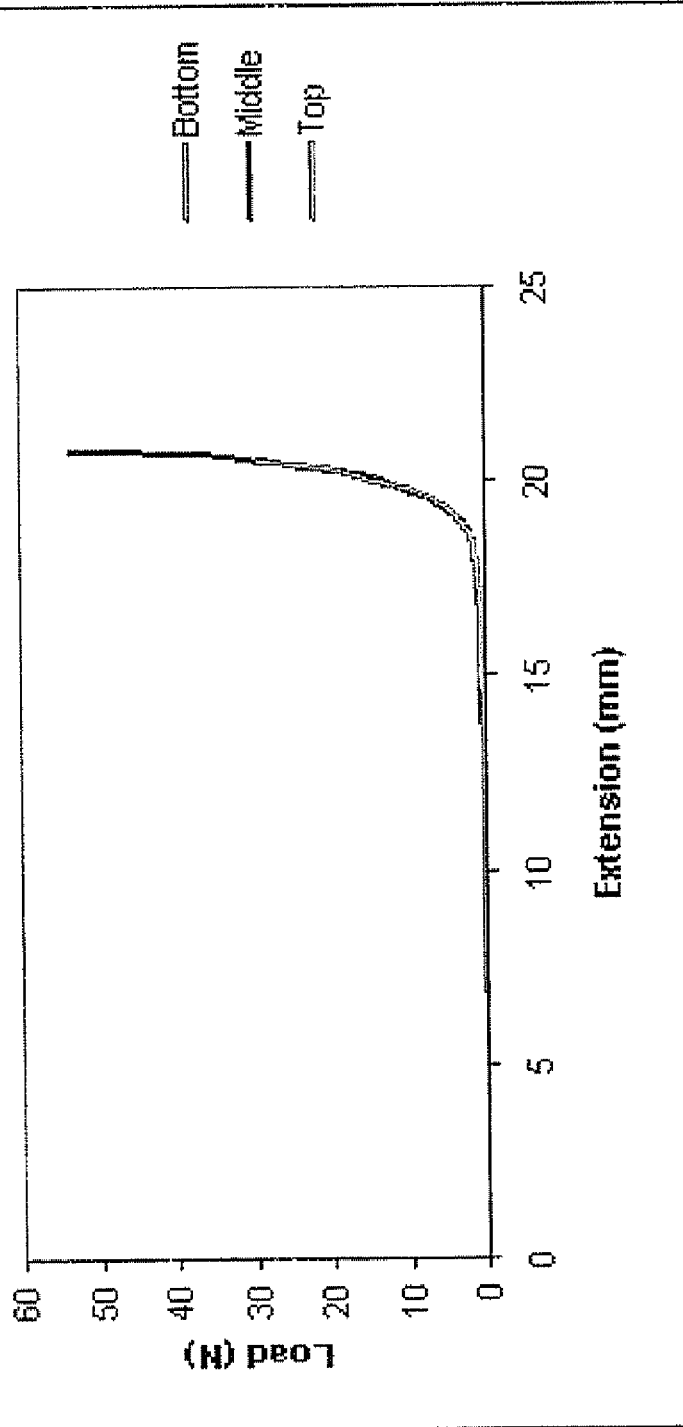
FIG. 4 is a graph showing SPH mechanical property and homogeneity for a p(HEMA)-based SPH synthesized at a starting reaction temperature of 60° C., and swelling for 0.5 hours in a simulated gastric fluid swelling medium.

FIG. 4 is a graph showing the results of an evaluation of a pHEMA SPH prepared by the method described above. Swelling of the SPH was performed using simulated gastric fluid at a pH of 1.0 at 37° C. for 0.5 hr. The SPH was prepared at a starting reaction temperature of 60° C. The SPH, once formed, was tested using a Chatillon TCD-200 digital mechanical tester.

Testing of the SPH was as follows: a cylindrical dehydrated SPH sample was placed into SGF at 37° C. for about 0.5 hrs. The fully swollen gel was subjected to the mechanical testing. Top, middle and bottom parts of the swollen gel were tested and proved to offer same mechanical properties under compression.

Figure 5:
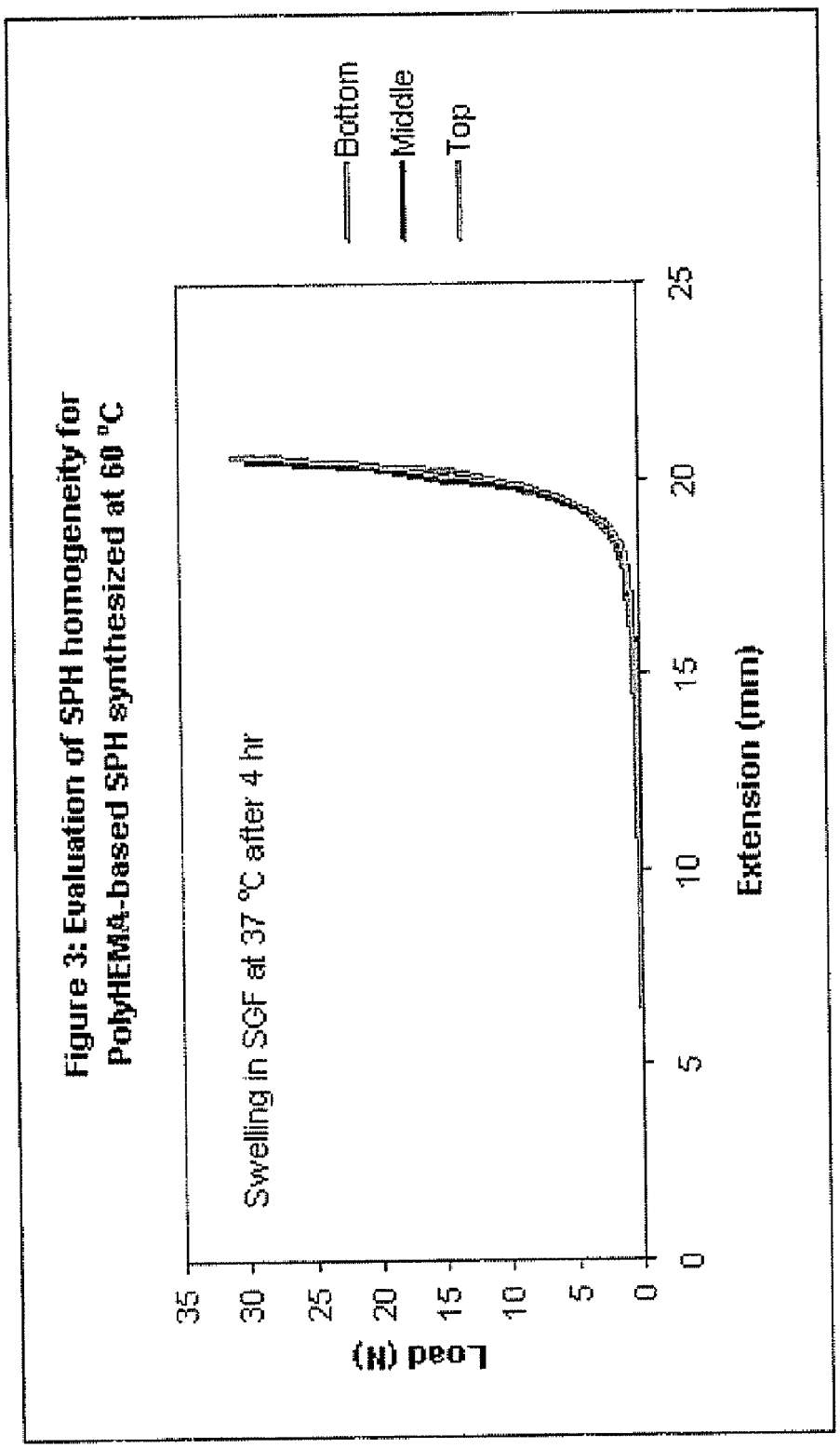
FIG. 5 is a graph showing SPH mechanical property and homogeneity for a p(HEMA)-based SPH synthesized at a starting reaction temperature of 60° C., and swelling at 37° C. for 4 hours in a simulated gastric fluid swelling medium.

FIG. 5 is a graph showing the results of an evaluation of a pHEMA SPH prepared by the method described above. Swelling of the SPH was performed using simulated gastric fluid at a pH of 1.0 at 37° C. for 4 hr. The SPH was prepared at a starting reaction temperature of 60° C. The SPH once formed, was tested using a Chatillon TCD-200 digital mechanical tester.

Testing of the SPH was as follows: a cylindrical dehydrated SPH sample was placed into SGF at 37° C. for about 4 his. The fully swollen gel was subjected to the mechanical testing. Top, middle and bottom parts of the swollen gel were tested and proved to offer same and stable mechanical properties under compression.

Example 2

Low Temperature Preparation of a Superporous Hydrogel

All reaction mixture components in the following example were used in the amounts indicated in Table 2.

Using a standard Pyrex glass tube, HEMA, PEGDA, acrylic acid, acetic acid, Pluronic® F127, tetramethylethylene diamine (TMED), and deionized water were mixed together at 25° C. After 2 minutes, APS and solid SBC were added with continuous mixing to evenly disperse the foaming agent (SBC) and initiator (APS) until a foam began to form. When the reaction was complete (about 11 minutes), as evidenced by the temperature and foam height remaining constant, a 5 wt % aluminum chloride solution was added and the hydrogel was equilibrated by rubbing to reach its swollen state. Foam height was about 3 cm. The SPH formed is very tough. During hydration, the transition from glass to rubber is very sharp, while overall the swelling is very slow, resulting in a hydrated SPH that is very durable.

TABLE 2

| Component | Amount |
|---|---|
| HEMA | 2000 μL |
| PEGDA | 40 μL |
| Acrylic acid | 50 μL |
| Acetic acid | 40 μL |
| Pluronic ® F127, 10% (aq) | 250 μL |
| TMED, 40 v/v %, (aq) | 65 μL |
| DI Water | 200 μL |
| APS, 40 wt % (aq) | 65 μL |
| SBC | 300 mg |

Example 3

High Temperature Preparation of a Superporous Hydrogel

All reaction mixture components in the following example were used in the amounts indicated in Table 2.

Using a standard Pyrex glass tube, HEMA, PEGDA, acrylic acid, acetic acid, Pluronic® F127, tetramethylethylene diamine (TMED), deionized water, APS, and SBC were thoroughly mixed. After mixing, the glass tube was placed into a water bath at 60° C. and, using a spatula, SBC dispersion was continued until a foam started to form. The tube was left in the bath until the foam was set (about 4-5 min). Foam height was about 7 cm. The formed SPH was treated in 5 wt % aluminum chloride solution for 30 min. The SPHs formed at 60° C. show more plastic (slow recovery) behavior in their swollen state than those formed at 25° C., while the SPHs formed at 25° C. are more elastic (fast recovery).

Figure 7:
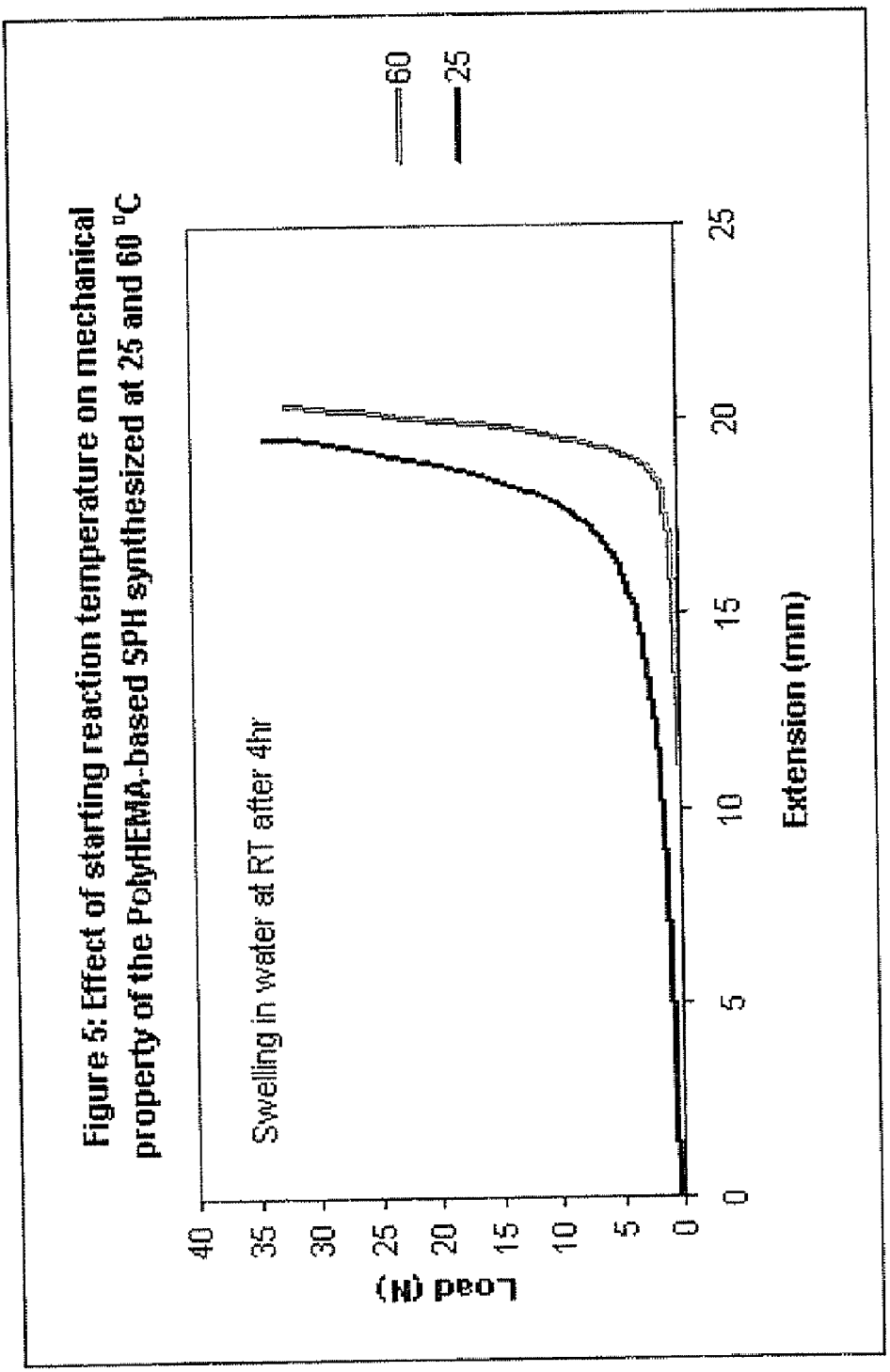
FIG. 7 is a graph showing the effects of different starting reaction temperatures on the mechanical properties of a p(HEMA)-based SPH, in a deionized water swelling medium at 22-25° C. for 4 hours.

FIG. 7 illustrates the difference in polyHEMA SPH strength based on the temperature at which the SPH formation is started. The polyHEMA SPH was prepared at a starting reaction temperature of 25° C. or 60° C., as indicated. The SPH was tested using a Chatillon TCD-200 digital mechanical tester. The SPH was swollen using deionized water as the swelling medium at a temperature of 22-25° C. The SPH was retained in the swelling medium for 4 hrs.

Testing of the SPH was as follows: a cylindrical dehydrated SPH sample was placed into water at RT for about 4 hrs. The fully swollen gel was subjected to the mechanical testing. Top, middle and bottom parts of the swollen gel were tested and proved to offer the same mechanical properties under compression. The polyHEMA SPH synthesized at higher temperature is softer, deforms to a greater extent than the polyHEMA SPH formed at the lower temperature, but it is still very strong. In addition, the polyHEMA SPH synthesized at the higher temperature has faster swelling kinetic, which is very desirable property.

Figure 8:
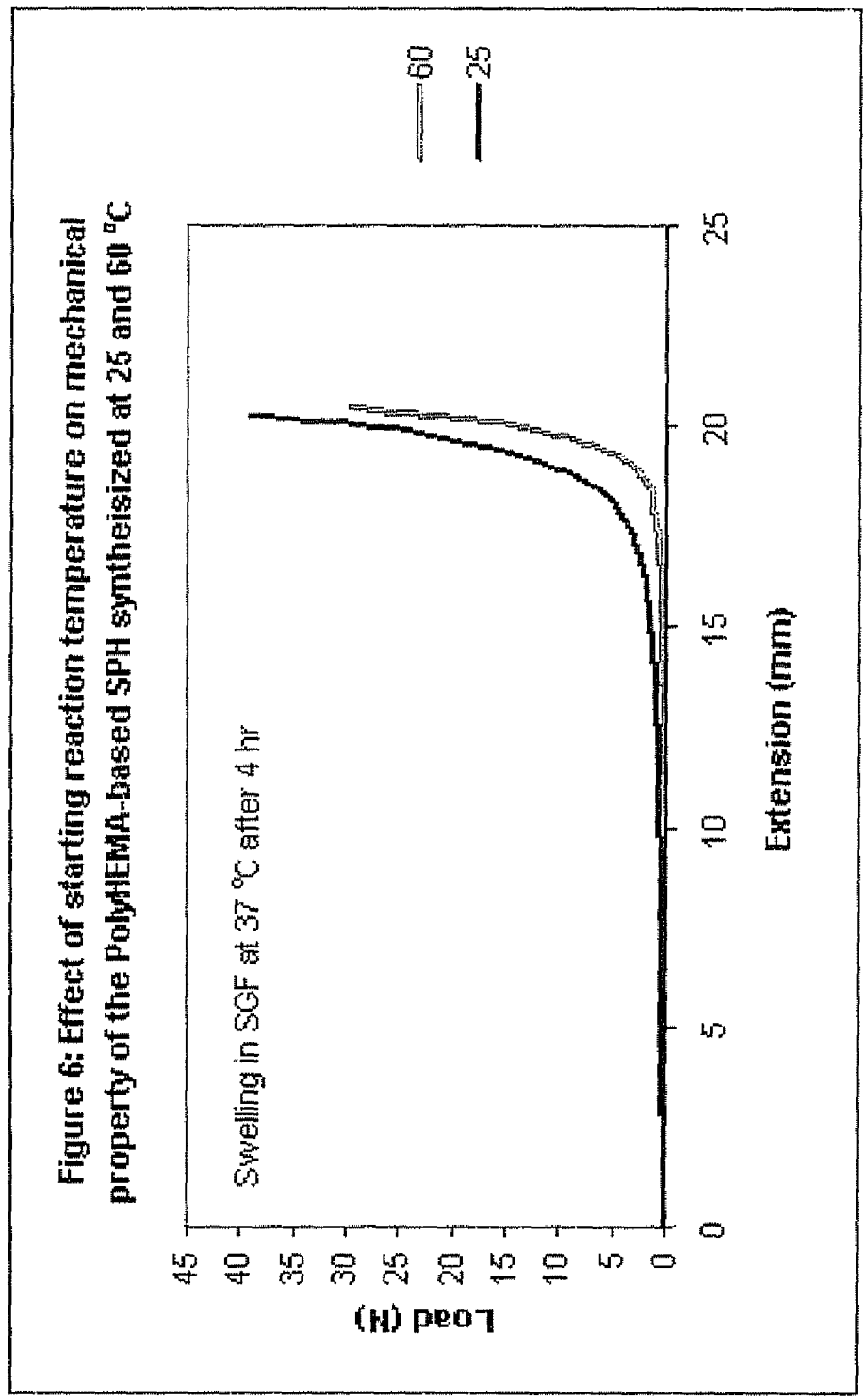
FIG. 8 is a graph showing the effects of different starting reaction temperatures on the mechanical properties of a p(HEMA)-based SPH, in a simulated gastric fluid swelling medium.

FIG. 8 illustrates the difference in polyHEMA SPH strength based on the temperature at which the SPH formation is started. The polyHEMA SPH was exposed to the same reaction conditions as was the polyHEMA SPH of FIG. 7, except that it was swollen in simulated gastric fluid at a pH of 1.0 at 37° C. for 4 hr. The polyHEMA SPH synthesized at a higher temperature is softer, deforms more but still is very strong. The mechanical behavior of the gels synthesized at different temperatures was found to be very stable in both SGF and deionized water (see FIG. 7).

The properties of the polyHEMA SPH are dependent on the starting reaction temperature, water content of the reacting mixture, and the foaming aid (e.g., acetic acid) concentration within the formulation. Higher temperature, higher water content, and higher acid concentration result in taller foam, smaller pore size, more flexibility, more processability, and better swelling properties (see FIGS. 7-8).

Figure 10:
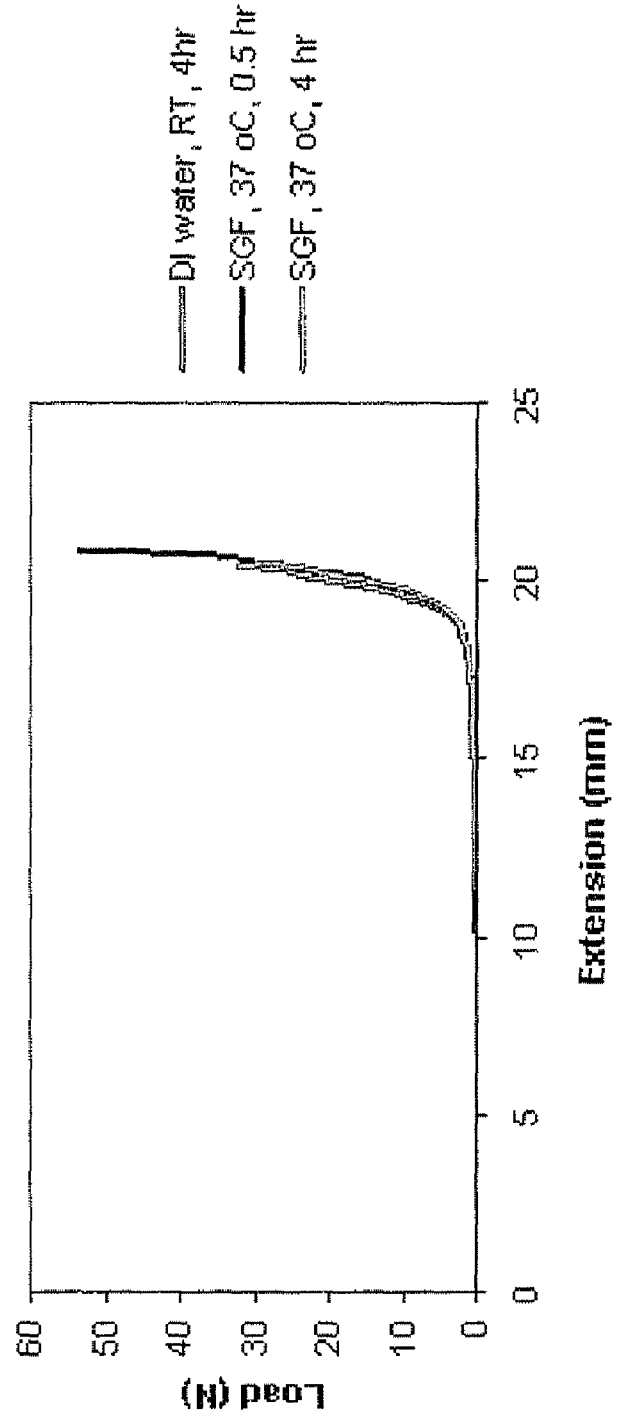
FIG. 10 is a graph showing the effects of different swelling media on the mechanical properties of a p(HEMA)-based SPH synthesized at 60° C.
Figure 11:
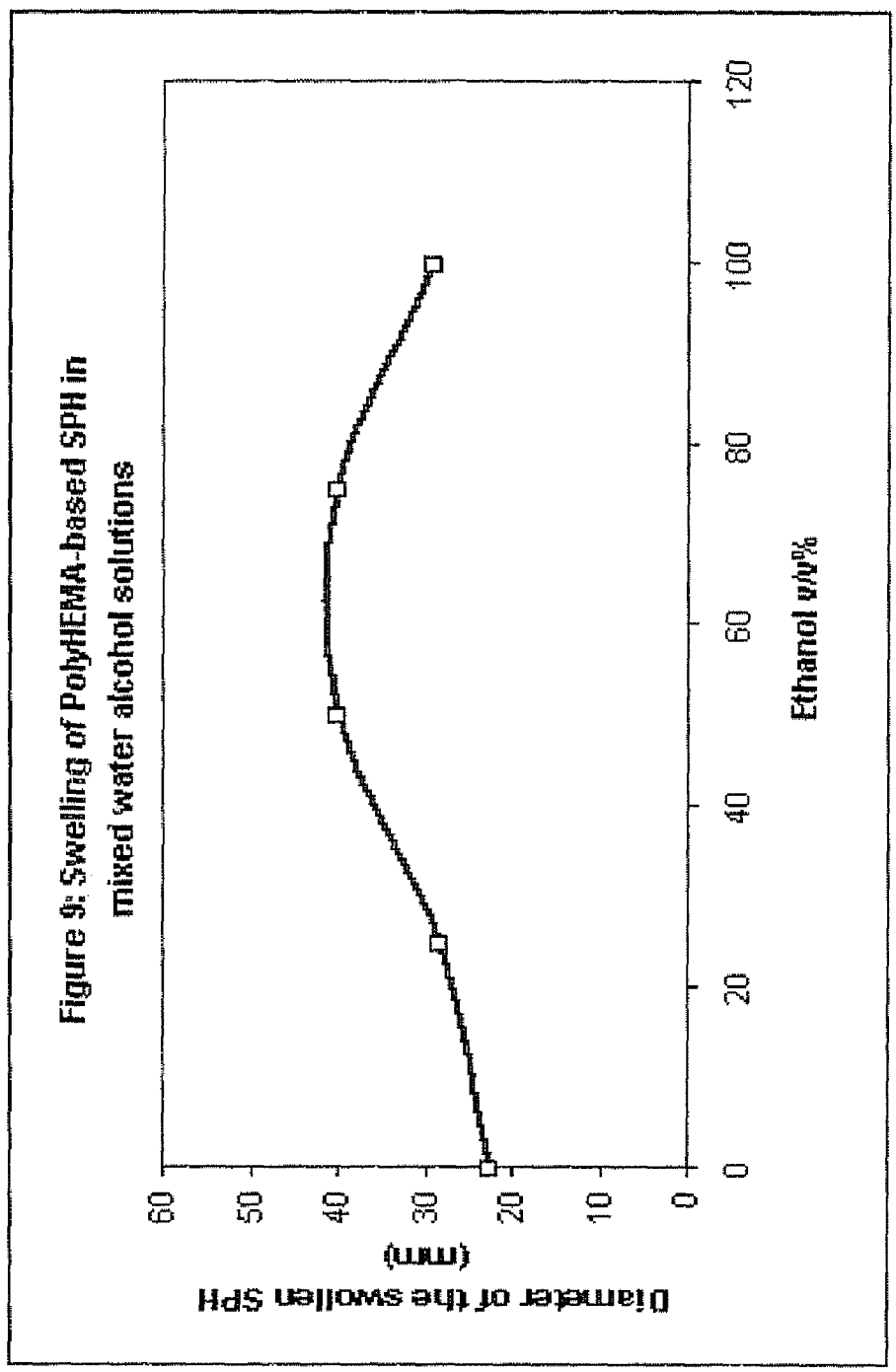
FIG. 11 is a graph showing the alcohol absorption capabilities of a p(HEMA)-based SPH.

FIGS. 3 and 7 illustrate that the mechanical strength of the prepared polyHEMA SPHs at high temperature is pH independent. FIGS. 4, 5, and 10 show that the polyHEMA SPH illustrates the same mechanical properties when retained in a low pH swelling medium for 4 hours and 0.5 hours. This indicates that polyHEMA SPHs of the present invention in their acid-swollen state are very stable in terms of their physical and mechanical properties. FIGS. 10 through 13 illustrate additional superior properties of the SPHs of the present invention. Of particular note, FIG. 11 illustrates the ability of the SPHs of the present invention to swell in the presence of alcohol, a property which is not normally exhibited in other hydrogels and which may have useful implications in drug delivery. The maximum alcohol absorption was found for the water/alcohol solution containing 60% alcohol.

Figure 12:
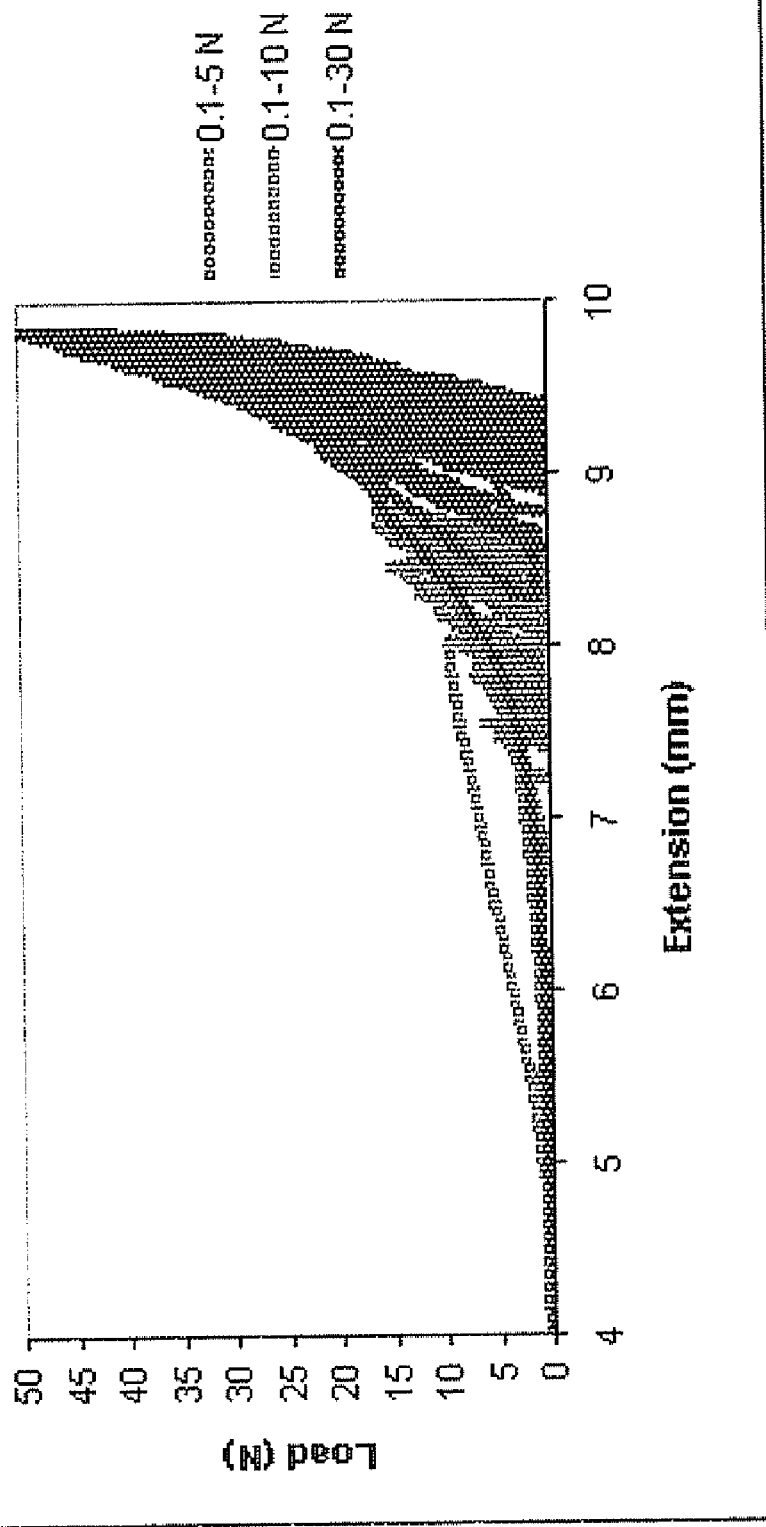
FIGS. 12 and 13 are graphs showing the effects of different cyclic compression loadings on the mechanical properties of a p(HEMA)-based SPEW
Figure 13:
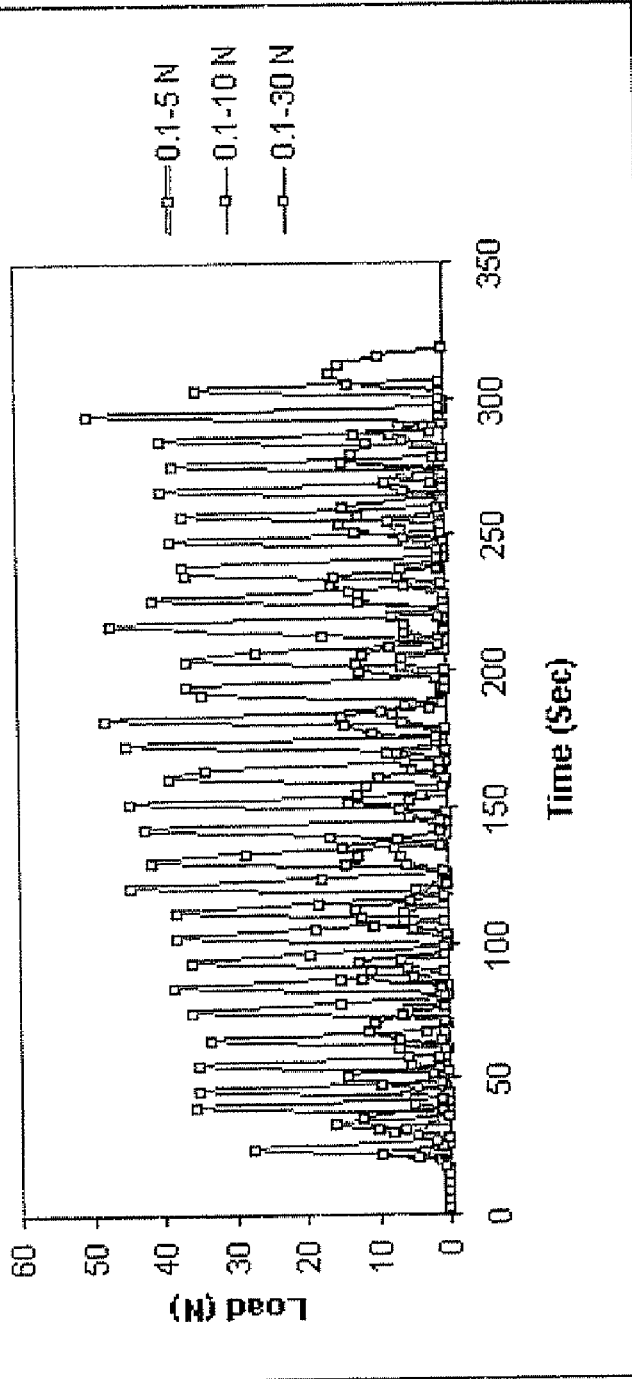
Figure 14:
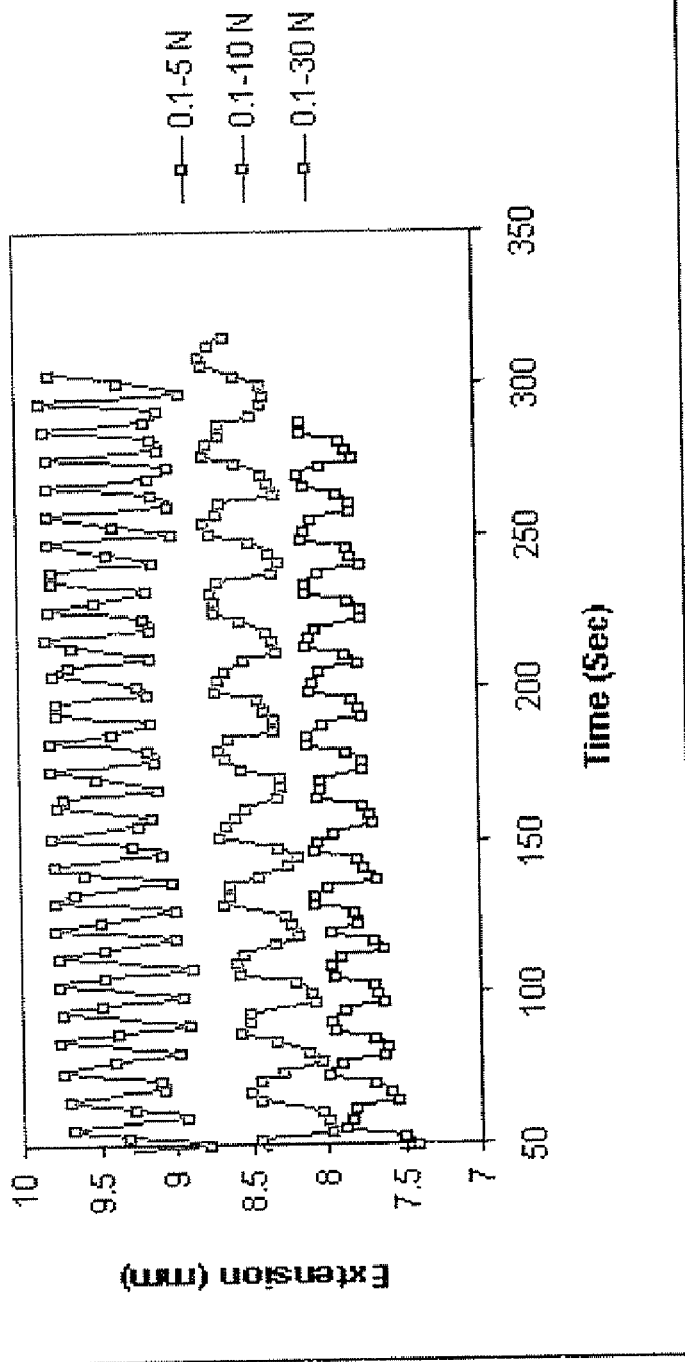
FIG. 14 is a graph showing the effects of different cyclic compression loadings on the deformation of p(HEMA)-based SPHs over time.

In addition, FIG. 12 indicates that the HEMA-based SPHs can withstand dynamic compression loadings applied to the swollen gel at different ranges. Only very tough superporous hydrogels can withstand 0.1-30 N compression cycles for extended period of time, as did the polyHEMA SPHs produced by the methods disclosed herein. FIG. 13 is a graph showing the load data of FIG. 12 plotted against time. FIG. 14 is a graph showing the effect of various loads on the extension of the polyHEMA SPHs over time.

Example 4

Figure 2:
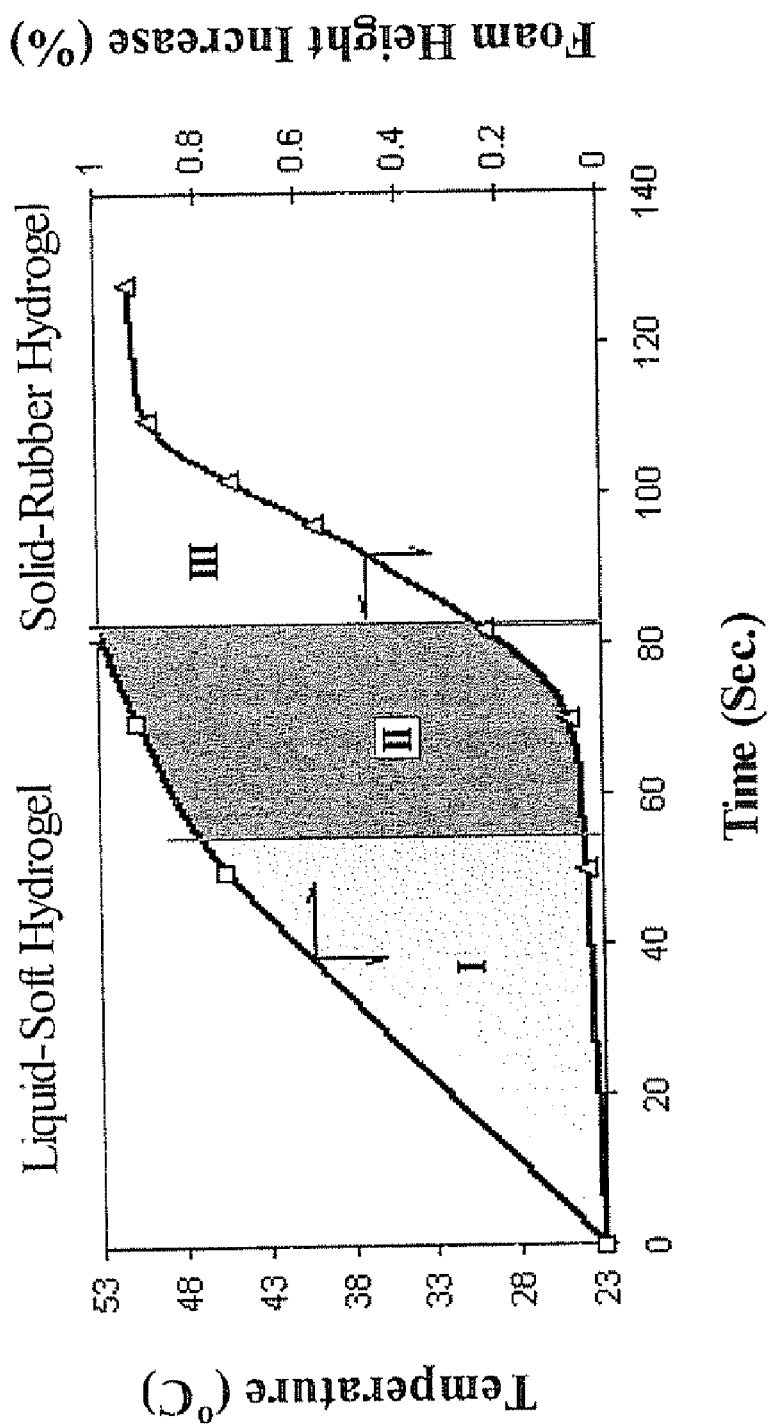
FIG. 2 is a graph showing profiles for temperature and foaming changes during a formation of a typical SPH of the invention initiated at room temperature. Square symbols (□) in the chart denote the degree of foaming and triangular symbols (Δ) indicate the reaction temperature.

Formation of a Superporous Hydrogel by Controlling the Addition of a Foaming Agent Separate aqueous solutions of monomer (e.g., HEMA), co-monomer (if used, e.g., HEA and acrylic acid), crosslinker (e.g., PEGDA), and foam stabilizer (e.g., F127) are prepared and combined with a foaming aid (e.g., acetic acid) and additional water under very gentle mixing conditions. Separate solutions of initiators (solutions of reductant and oxidant, e.g., TMED and APS, respectively) are each added and well dispersed (approximately 10 to 15 seconds). Shortly after (approximately 20 seconds), the reaction mixture is homogenized, the foaming agent (e.g., SBC) is added and evenly dispersed. All additions normally take place at room temperature (about 20-25° C.) and under ambient atmospheric conditions. Dissolution of the foaming agent increases the pH of the reaction medium to a level at which the initiator decomposes faster. As the formation of initiator radicals reaches a certain level, the polymerization reaction proceeds rapidly and the reacting mixture becomes viscous over time. Dissolution of the foaming agent also promotes its interaction with the foaming aid to produce gases required for the blowing process. The two processes are conducted in such a way as to enable controlled foaming and polymerization. As shown in FIG. 2, t=0 is the time at which the foaming agent was added, (□) symbols in the chart denote the degree of foaming, and (Δ) symbols denote the temperature rise during the reaction. At stage I of this process, about 80% of the foaming occurs while the polymerization/gelation process has not substantially begun, as indicated by the insignificant rise in the reaction mixture temperature. At stage II, the remainder of the foaming process takes place as the reaction temperature begins to increase (by about 5° C. to about 10° C.). The foam consistencies at stages I and II are a fluid and a soft solid, respectively. With no foam development beyond this point (Stage III), the polymerization proceeds and foam turns to a solid flexible rubber as the reaction temperature is maximized During the polymerization process, there is progressive change from a liquid to a low-viscous oil to a high viscous oil and finally to a solid flexible rubber. The polymerization reaction is usually complete by about 10 minutes after the addition of foaming agent.

A high or very high mechanical property can be achieved with SPHs in their fully-swollen state, if the SPH has a very homogeneous porous structure, as we have achieved. A swollen SPH quickly fails under static and dynamic mechanical loading (compression, tension, bending, twisting) if the SPH possesses weak points like big pores, pores of different sizes or areas of different porosity (non-porous versus porous). A premature gelation before foaming, results in formation of hydrogel product lacking significant porosity rather than a superporous hydrogel rich in porosity. On the other hand, a premature extensive foaming before gelation results in heterogeneous pore structure and size. The method in which a foaming agent is added to the reaction mixture, its mixing with the reaction mixture, the reaction temperature, and the amount of diluent, foaming aid, and/or foam stabilizer are critical factors to achieve harmonized foaming and gelation reactions.

Example 5

Modified PolyHEMA-Based Superporous Hydrogels

Several SPHs useful in gastric retention and based on the monomer 2-hydroxyethylmethacrylate were produced. PolyHEMA SPHs are strong, demonstrating the ability to resist contractions imposed by the stomach of the patient, and exhibit excellent swelling properties, including a fast rate of swelling and the ability to absorb a large volume of fluid. For oral drug delivery purposes, the SPHs need to be encapsulated in an orally administrable capsule (gelatin, HPMC for example). The encapsulation of PolyHEMA SPHs requires a further step of plasticization including use of external/internal plasticizers as well as moisture. The general practice with external plasticizers is to soak the final purified and dried SPH in the plasticizer solution. By this method, the plasticizer molecules will be incorporated in between the polymer chains and help them with better movement, which results in more flexibility. With internal plasticization, a monomer(s) having a very low glass transition temperature (like ethyl acrylate, ethyl methyl acrylate, butyl acrylate, and similar) will be incorporated into the structure of a high glass transition monomer like HEMA. In this way, and depending on the monomer composition, a flexible copolymer of low/high glass transition monomers will be formed with certain advantages and disadvantages over external plasticization.

Example 6

Preparation of HEMA-Based Superporous Hydrogels using HEA as an Internal Plasticizer All reaction mixture components in the following example were used in the amounts indicated in Table 3 (volumes are given in μLs and the weights in mgs).

Using a standard Pyrex glass tube, monomers of HEMA and HEA were combined with PEGDA, acrylic acid, acetic acid, Pluronic® F127, deionized water, tetramethylethylene diamine (TMED), APS, and SBC and thoroughly mixed. After mixing, the glass tube was placed into a water bath at 70° C. and, using a spatula, SBC dispersion was continued until the reaction mixture began to foam. In order to optimize the swelling and mechanical properties of the HEMA-based SPH, the HEA concentration was varied in the range of HEA/HEMA ratio of 0-50 v/v %. From the hydrogels produced in this example, optimal properties for a superporous hydrogel to be used as an oral drug delivery vehicle were achieved when the HEA/HEMA ratio was around 25 v/v % or less (e.g., F-1, F-2, and F-3). Increasing the amount of HEA incorporated into the SPH produced SPHs that exhibit higher swelling, more flexibility, and faster absorption but lower mechanical properties compared to the control, which is based on pure HEMA, SPHs prepared with at least 80% HEMA and 20% HEA exhibited optimum properties.

Figure 6:
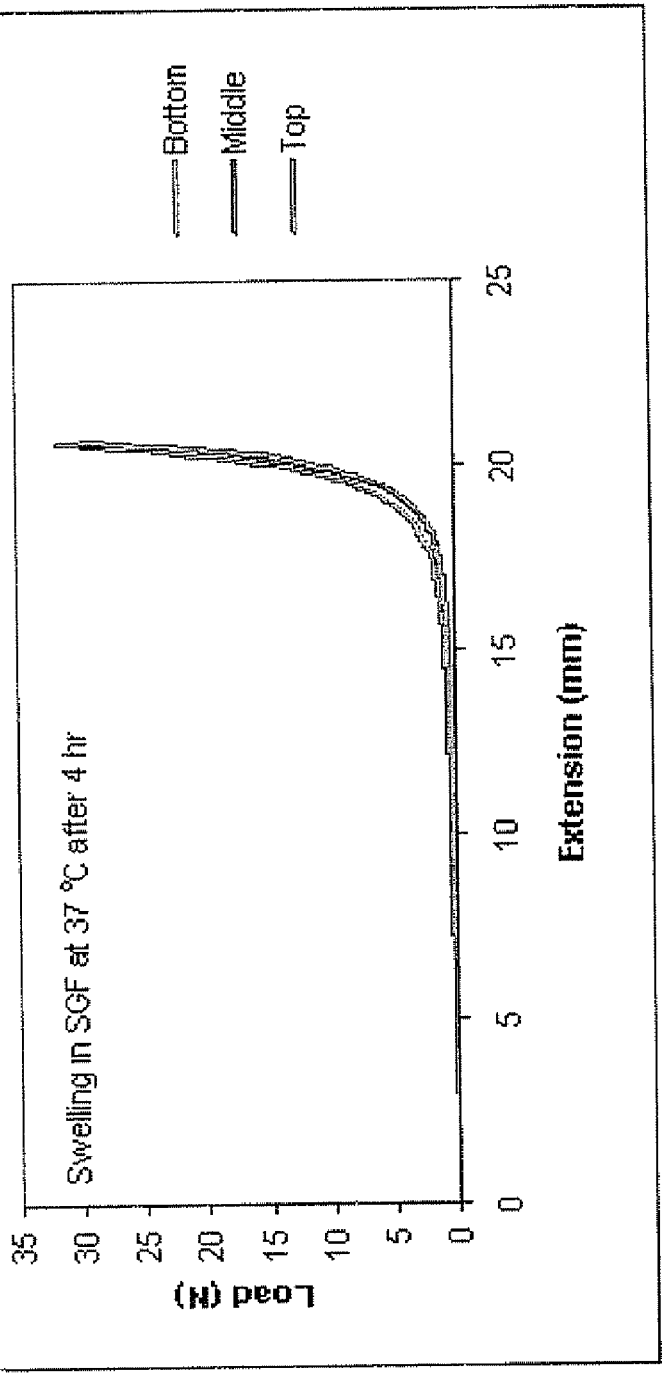
FIG. 6 is a graph showing SPH mechanical property and homogeneity for a p(HEMA/HEA)-based SPH synthesized at a starting reaction temperature of 60° C., and swelling at 37° C. for 4 hours in a simulated gastric fluid swelling medium.

FIG. 6 illustrates the homogeneity of the polyHEMA/HEA SPH under compression. Swelling of the polyHEMA/HEA SPH was performed using simulated gastric fluid at a pH of 1.0 at 37° C. for 4 hi. The polyHEMA/HEA SPH was prepared at a starting reaction temperature of 60° C. The SPH, once formed, was tested using a Chatillon TCD-200 digital mechanical tester.

Testing of the SPH was as follows: a cylindrical dehydrated SPH sample was placed into SGF at 37° C. for about 4 hrs. The fully swollen gel was subjected to the mechanical testing. Top, middle and bottom parts of the swollen gel were tested and proved to offer same and stable mechanical properties under compression.

Figure 9:
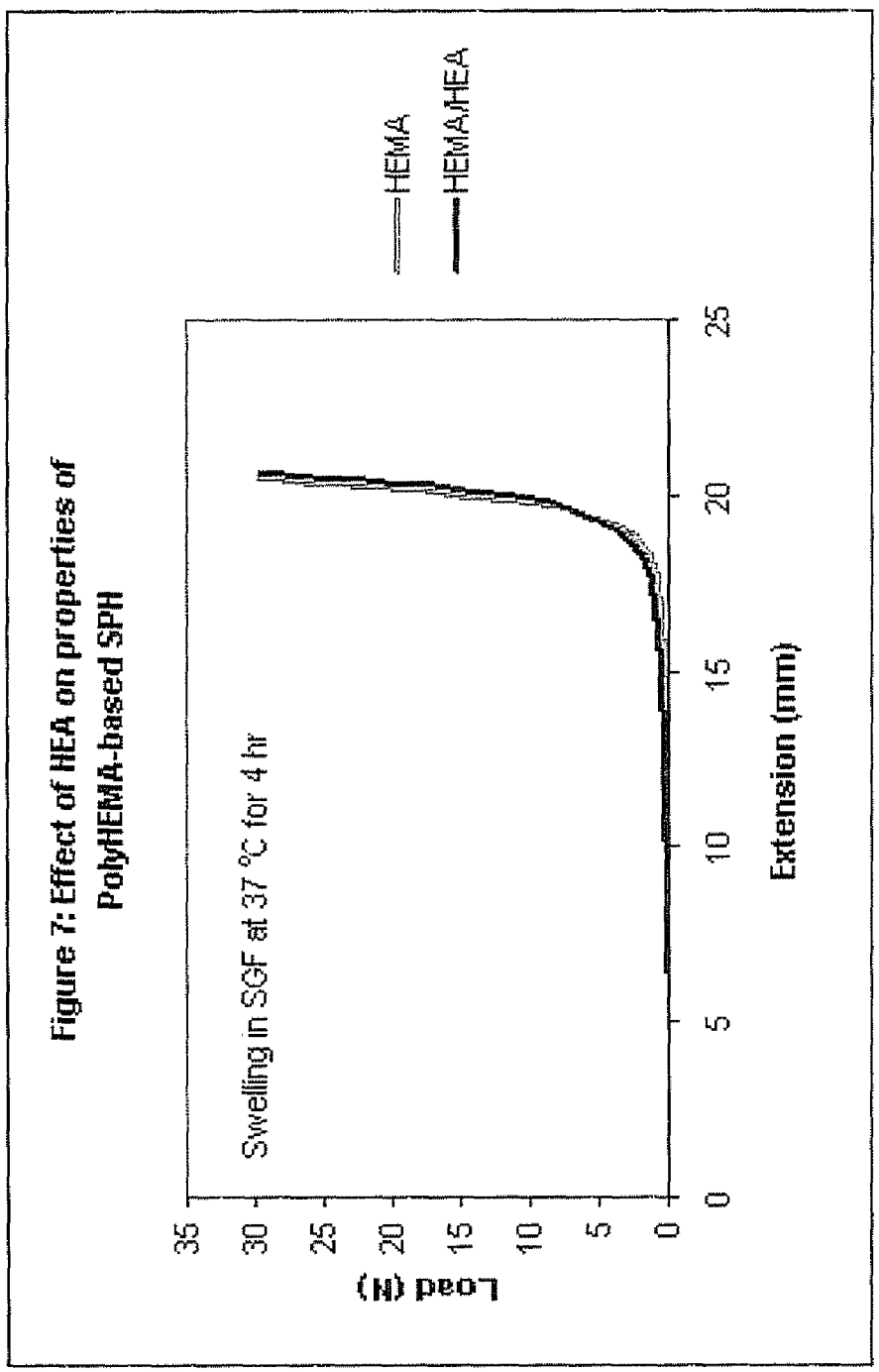
FIG. 9 is a graph showing the effects of using HEA as a co-monomer on the mechanical properties of a p(HEMA)-based SPH.

FIG. 9 illustrates the different mechanical properties of a HEMA-based SPH and a polyHEMA/HEA SPH of the present invention (lower HEA concentration). As indicated, both SPHs exhibit similar excellent mechanical properties at a pH of 1.0 (simulated gastric fluid) after retention for 4 hours. The polyHEMA deformed slightly less than the polyHEMA/HEA.

A wide range of SPHs having diverse mechanical properties can be prepared using mixed monomers of HEMA and HEA. While HEMA is responsible for the improved high mechanical properties of the SPH, the HEA provides better swelling properties, including an increase in the swelling rate and swelling capacity.

Without affecting the mechanical properties, a flexibilized type of SPH can be obtained if the HEMA monomer is partially replaced by HEA as comonomer. High temperature, high water content, and high HEA concentration all result in more flexibility in dry and in water-swollen state. Increasing the HEA concentration produces a SPH having superior swelling properties at the expense of its mechanical properties. While the HEA concentration can be preferably varied in the range of HEA/HEMA ratio of 0-50 v/v %, the most preferable concentration is around 25 v/v % ratio or less of HEA/HEMA. In a preferred embodiment, the ratio of HE-A to HEMA is 20 v/v %.

TABLE 3

Examples of Flexibilized HEMA-Based SPHs using HEA as a Comonomer

| Component | F-1 | F-2 | F-3 | F-4 |
|---|---|---|---|---|
| HEMA (μL) | 2000 | 2000 | 2000 | 2000 |
| HEA (μL) | — | 200 | 500 | 1000 |
| PEGDA (μL) | 40 | 40 | 40 | 40 |
| Acrylic acid (μL) | 50 | 50 | 50 | 50 |
| Acetic acid (μL) | 40 | 40 | 40 | 40 |
| Pluronic ® F127, 10% (aq) (μL) | 250 | 250 | 250 | 250 |
| Water (μL) | 250 | 250 | 250 | 250 |
| TMED, 40 v/v % (aq) (μL) | 65 | 65 | 65 | 65 |
| APS, 40 wt % (aq) (μL) | 65 | 65 | 65 | 65 |
| SBC (mg) | 300 | 300 | 300 | 300 |
| Diameter in the swollen state in aqueous 5 wt % AlCl$_3$ solution, mm | about 20 mm | about 22 mm | about 25 mm | about 27 mm |
| Absorption rate | Very slow | Faster than F1 | Faster than F-2 | Faster than F-3 |
| Mechanical property | Very strong | Strong | Medium strong | Medium |

Example 7

Preparation of HEMA-Based Superporous Hydrogels using Poly(ethylene glycol) as an External Plasticizer Different dry SPH samples were placed into warm solutions of 10% PEG-600, 10% PEG-1450, 10% PEG-4000, as well as mixtures of different grades; 5% PEG-600/5% PEG-1450 and 5% PEG-1450/5% PEG-4000. For comparison, samples were also put into water and a solution of 10% glycerin.

The samples were left in solution for a few days to absorb the plasticizer. After drying, the samples were manually tested with the objective of finding the best working plasticizer combination with the highest average molecular weight to avoid leaching. It was found that lower molecular weight PEGs are very effective. Nevertheless, the final dosage form for human administration via encapsulation requires a hydrophobic coating to prevent the interaction of plasticizer and capsule.

Example 8

Preparation of HEMA-Based Superporous Hydrogels using Moisture as a Processing Aid Samples of pHEMA-AAc/Al$^{3+}$ containing different amounts of aluminum were put into an oven at 95% humidity and 40° C. After a short time (about 1 hour), they were removed and manually tested for hardness. They were put back into the oven and incubated overnight. They were again removed and manually tested for hardness. Finally, the pHEMA-AAc/Al$^{3+}$ SPHs were left in ambient conditions for a few days and manually tested for hardness again.

Samples that were put into a humid oven quickly became soft. They were softened within one hour of being put into the oven and were still soft upon later removal from the oven. The process of moisture absorption can be catalyzed by incorporating moisture absorptive materials into the SPH structure. These include, for example, silica gel, superdisintegrants, and super water absorbents. PolyHEMA SPHs can be encapsulated at conditions where relative humidity and temperature of the environment are favorable for SPH plasticization to occur.

From the foregoing description, it will be apparent that variations and modifications may be made to the invention described herein to adopt it to various applications and conditions. Such embodiments are also within the scope of the following claims.

All patents, patent application publications, and other publications mentioned in this specification are herein incorporated by reference to the same extent as if each independent publication or patent application was specifically and individually indicated to be incorporated by reference.

What is claimed is:

1. A method of preparing a superporous hydrogel, said method comprising the steps of:
   a) preparing a mixture comprising an ethylenically-unsaturated monomer of hydroxyethyl methacrylate (HEMA), at least one cross-linking agent, and at least one property-modifying agent comprising an ion-complexable site, wherein said HEMA is present in said mixture in an amount greater than 80 wt %; and
   b) causing polymerization of said mixture by contacting said mixture with at least one polymerization agent to form said hydrogel.

2. The method of claim 1, wherein the property-modifying agent has an ion-complexable site comprising an ion selected from the group consisting of: H$^+$, Na$^+$, K$^+$, NH$_4^+$Ca$^{2+}$, Mg$^{2+}$, Ba$^{2+}$, Cu$^{2+}$, Zn$^{2+}$, Mn$^{2+}$, Fe$^{2+}$, Fe$^{3+}$, Cr$^{3+}$, Al$^{3+}$, and Ce$^{4+}$.

3. The method of claim 1 further comprising:
   c) reacting said hydrogel with one or more ions selected from the group consisting of H$^+$, Na$^+$, K$^+$, NH$_4^+$Ca$^{2+}$, Mg$^{2+}$, Ba$^{2+}$, Cu$^{2+}$, Zn$^{2+}$, Mn$^{2+}$, Fe$^{2+}$, Fe$^{3+}$, Cr$^{3+}$, Al$^{3+}$, and Ce$^{4+}$ under equilibrating conditions.

4. The method of claim 1 wherein the mixture of step a) further includes one or more of a diluent, a foaming agent, a foaming aid, and a foam-stabilizer.

5. The method of claim 1, wherein said polymerization agent comprises a thermal initiator or an agent that produces an oxidation-reduction reaction.

6. The method of claim 4, wherein said foaming agent promotes foaming upon chemical reaction with an acid or upon decomposition and release of a gas during said decomposition.

7. The method of claim 1, wherein:
   (i) the mixture of step a) further comprises a foaming agent and a foaming aid, wherein the foaming agent reacts with the foaming aid within between 5 and 15 seconds after the addition of said foaming agent to the mixture; or
   (ii) the mixture of step a) further comprises one or more ethylenically-unsaturated comonomers, which are present in said mixture in less than 20 wt %.

8. The method of claim 7, wherein said ethylenically-unsaturated comonomer is acrylic acid (AAc) and salts thereof, C1-6 alkyl esters of acrylic acid and salts thereof, methacrylic acid and salts thereof, C1-6 alkyl esters of methacrylic acid, acrylamide (AAm), C1-6 alkylamides of acrylic acid, C2-12 dialkylamides of acrylic acid, N-isopropylacrylamide (NIPAM), methacrylamide, C1-6 alkylamides of methacrylic acid, dialkylamides of methacrylic acid, N-cyclopropyl methacrylamide, N,N-dimethylarninoethyl acrylate, acrylonitrile, 2-hydroxyethyl acrylate (HEA), ethyl acrylate, butyl acrylate, isodecyl methacrylate, methyl methacrylate, butyl methacrylate, lauryl methacrylate, stearyl methacrylate, 2-hydroxypropyl acrylate, 2-hydroxypropyl methacrylate (HPMA), butanediol monoacrylate, itaconic acid, N-vinyl pyrrolidone (VP), N,N-dimethylaminoethyl acrylate, diallyldimethylammonium chloride (DADMAC), 2-(methacryloyloxy)ethyl trimethylammonium chloride, 2-acrylamido-2-methyl-1-propanesulfonic acid (AMPS), potassium 3-sulfopropyl acrylate (SPAK), potassium 3-sulfopropyl methacrylate (SPMAK), or 2-(acryloyloxyethyl)trimethylammonium methyl sulfate (ATMS).

9. The method of claim 7, wherein said mixture comprises acrylic acid and HEA as comonomers.

10. The method of claim 1, wherein said crosslinking agent is N, N'- methylenebisacrylamide (BIS), N,N'-ethylenebisacrylamide (EBA), polyethylene glycol diacrylate (PEGDA), polyethylene glycol dimethacrylate (PEGDMA), ethylene glycol diglycidyl ether, alkoxylated cyclohexanedimethanol diacrylate, dipentaerythritol pentaacrylate, ethoxylated (9) trimethylolpropane triacrylate, ethoxylated (15) trimethylolpropane triacrylate, methoxy polyethylene glycol (550) monomethacrylate, ethoxylated hydroxyethyl methacrylate, methoxy polyethylene glycol (350) methacrylate, glycidyl methacrylate, polyamidoamine epichlorohydrin resin, trimethylolpropane triacrylate (TMPTA), piperazine diacrylamide, glutaraldehyde, or epichlorohydrin.

11. The method of claim 4, wherein said diluent is deionized water (DI), ethyl alcohol, isopropyl alcohol (IPA), or a water miscible organic solvent in water.

12. The method of claim 4, wherein said foaming aid is an organic or inorganic acid selected from acrylic acid, citric acid, acetic acid, hydrochloric acid, phosphoric acid, carbonic acid, boric acid, sulfuric acid, p-toluene sulfonic acid, nitric acid, hydrobromic acid, and chloric acid.

13. The method of claim 4, wherein said foaming agent is a carbonate, a bicarbonate, or a salt thereof, or an azo compound.

14. The method of claim 3, wherein said mixture comprises a chelating agent selected from a monovalent, a bivalent, and a trivalent ion salt.

15. The method of claim 14, wherein said chelating agent is selected from potassium chloride, calcium chloride, and aluminum chloride.

16. The method of claim 1, wherein the property-modifying agent is selected from a monomer, a polymer, or a polyphenolic complexing agent.

17. The method of claim 16, wherein the monomer is an acrylic acid.

18. The method of claim 16, wherein the polymer comprises one or more of the following:
   (a) a polysaccharide selected from alginate and derivatives thereof, chitins, chitosan and derivatives thereof, cellulose and derivatives thereof, starch and derivatives thereof, cyclodextrin, dextran and derivatives thereof, gums, lignins, pectins, saponins, deoxyribonucleic acids, and ribonucleic acids;
   (b) a polymer, a polypeptide, or protein selected from albumin, bovine serum albumin, casein, collagen, fibrinogen, gelatin and derivatives thereof, gliadin, sodium glycine carbonate, bacterial cell membrane enzymes, and a poly(amino acid); or
   (c) a homo- or co-polymer comprised of one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone.

19. The method of claim 18, wherein the poly(amino acid) is selected from polyproline, poly(L-arginine), poly(L-lysine), polysarcosine, poly(L-hydroxyproline), poly(glutamic acid), poly(S-carboxymethyl-L-cysteine), and poly(aspartic acid).

20. The method of claim 16, wherein the polyphenolic complexing agent is selected from the group consisting of gallotannins, ellagitannins, taragallotannins, caffetannins, proanthocyanidins, catechin, epicatechin, chlorogenic acid, and arbutin.

21. The method of claim 1, wherein the property-modifying agent comprises one or more of the following:
  (a) a natural or synthetic polyelectrolyte, a hydrophilic polymer having a net neutral charge and a molecular weight in the range of 400 Da to 40 kDa, or a molecule having a reacting group capable of forming a complex with an ion;
  (b) carboxymethylcellulose, alginate, starch glycolate, carboxymethyl starch, dextran, pectinate, xanthan, carrageenan, gellan, hyaluronic acid, and pectinic acid, or a salt thereof, wherein the salt comprises a counterion selected from the group consisting of: $Na^+$, $K^+$, $NH_4^+$ $Ca^{2+}$, $Mg^{2+}$, $Ba^{2+}$, $Cu^{2+}$, $Zn^{2+}$ and $Mn^{2+}$; or
  (c) poly(acrylic acid) or a salt thereof, poly(methacrylic acid) or a salt thereof, polyacrylamide, polystyrene sulfonate), poly(aspartic acid), polylysine, CARBOPOL, or ultramylopectin.

22. The method of claim 21, wherein said reacting group capable of forming a complex with an ion is a carboxyl group capable of complexing with a calcium, iron, or aluminum ion.

23. The method of claim 3, wherein, after step (c), said hydrogel may further be treated with one or more ions selected from the group consisting of: $H^+Na^+$, $K^+$, $NH_4^+Ca^{2+}$, $Mg^{2+}$, $Ba^{2+}$, $Cu^{2+}$, $Zn^{2+}$, $Mn^{2+}$, $Fe^{2+}$, $Fe^{3+}$, $Cr^{3+}$, $Al^{3+}$, and $Ce^{4+}$ under equilibrating conditions.

24. The method of claim 3, wherein the temperature of said mixture is maintained at between:
  (i) 20° C. and 80° C. during step (c);
  (ii) 20° C. and 60° C. during step (c); or
  (iii) 20° C. and 40° C. during step (c).

25. The method of claim 1, wherein said polymerization occurs at a temperature in the range of:
  (i) 20° C. to 100° C.;
  (ii) 55° C. to 75° C.; or
  (iii) 30° C. to 60° C.

26. The method of claim 4, wherein said foaming agent is added as a solid mass; dissolved in an aqueous or organic/aqueous solvent system; dispersed in an organic solvent; coated with an organic compound such that dissolution of said foaming agent in water is delayed; encapsulated such that dissolution of said foaming agent in water is delayed; or dispersed in a monomer that participates in the superporous hydrogel polymerization.

27. The method of claim 1, wherein said polymerization comprises subjecting said mixture to foaming conditions substantially concurrently with gelation of said hydrogel.

28. The method of claim 1, wherein said hydrogel is dehydrated.

29. The method of claim 28, wherein said hydrogel is dehydrated by lyophilization.

30. The method of claim 28, wherein, following dehydration, said hydrogel is encapsulated.

31. The method of claim 28, wherein, following dehydration, said hydrogel is contacted with a plasticizer, moisture or both to form a plasticized hydrogel.

32. The method of claim 31, wherein plasticization is performed:
  (i) at a temperature greater than 40° C.; or
  (ii) at a humidity of greater than 60% relative humidity.

33. The method of claim 31, wherein the plasticized hydrogel is encapsulated in an orally-administrable capsule comprising gelatin or hydroxypropyl methylcellulose.

34. The method of claim 33, wherein the orally-administrable capsule contains a preventative layer that separates the plasticized hydrogel from the capsule.

35. The method of claim 34, wherein the coating agent is applied to the hydrogel prior to encapsulation.

36. The method of claim 31, wherein the hydrogel further comprises a fast moisture-absorptive agent that catalyzes plasticization of the hydrogel.

37. The method of claim 36, wherein plasticization is performed:
  (i) at a temperature greater than 40° C.; or
  (ii) at a humidity of greater than 60% relative humidity.

38. A superporous hydrogel prepared by the method of claim 1.

39. The hydrogel of claim 38, wherein said hydrogel is characterized as follows:
  (i) resistant to a compressive load of between 2 to 50 N;
  having a relative compressive strength that is 5-fold greater than the compressive strength of a superporous hydrogel lacking said property-modifying agent;
  (iii) able to maintain its mechanical integrity at a pH less than 5.0 for greater than 1 hour when in its fluid-swollen state;
  (iv) having a compressive strength at breaking point of the hydrogel, when in its fluid-swollen state, of between 1.0 kPa and 500 kPa.;
  (v) having an average pore size in the range of 1 μm to 5000 μm when in its dry state; and
  (vi) having an equilibrium volume swelling ratio in the range of 8 to 18.

40. The hydrogel of claim 39, wherein said hydrogel is able to maintain its mechanical integrity at a pH of less than 1.0 for greater than 1 hour when in its fluid-swollen state.

41. The hydrogel of claim 39, wherein said hydrogel is able to maintain its mechanical integrity at a pH of less than 5.0 for greater than 3 hours when in its fluid-swollen state.

42. A pharmaceutical composition in solid dosage form comprising a pharmacologically effective dose of a biologically active agent and a superporous hydrogel prepared by the method of claim 1.

43. The pharmaceutical composition of claim 42, wherein said biologically active agent is a drug, a nutritional supplement, a vitamin, or a fertilizer.

44. The pharmaceutical composition of claim 42, which said solid dosage form comprises a tablet, a capsule, particles, a wax, oil, granules, a film, a sheet, a fiber, a rod, or a tube.

45. A method for prolonged retention of a pharmaceutical agent by gastric retention comprising administering to a patient a superporous hydrogel prepared by the method of claim 1 comprising said pharmaceutical agent, wherein said hydrogel swells upon entering the stomach of the patient and extends release of said agent for at least one hour.

46. The method of claim 45, wherein the pharmaceutical agent is a drug, a nutritional supplement, or a vitamin.

* * * * *